(12) United States Patent
Nguyen et al.

(10) Patent No.: US 12,217,422 B1
(45) Date of Patent: Feb. 4, 2025

(54) COMPUTE SYSTEM WITH SKIN DISEASE IDENTIFICATION MECHANISM AND METHOD OF OPERATION THEREOF

(71) Applicant: BelleTorus Corporation, Cambridge, MA (US)

(72) Inventors: Tien Dung Nguyen, Toulouse (FR); Thang Duc Nguyen, Toulouse (FR); Folkert Blok, Toulouse (FR); Jonathan Wolfe, Plymouth Meeting, PA (US); Kavita Mariwalla, Oyster Bay, NY (US); Nga Thi Thuy Nguyen, Toulouse (FR)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 18/431,752

(22) Filed: Feb. 2, 2024

(51) Int. Cl.
*G06T 7/00* (2017.01)
*G06T 7/11* (2017.01)
*G16H 30/40* (2018.01)
*G16H 50/20* (2018.01)

(52) U.S. Cl.
CPC ............ *G06T 7/0012* (2013.01); *G06T 7/11* (2017.01); *G16H 30/40* (2018.01); *G16H 50/20* (2018.01); *G06T 2207/20084* (2013.01); *G06T 2207/30088* (2013.01)

(58) Field of Classification Search
CPC ............ G06T 7/0012; G06T 7/11; G06T 2207/20084; G06T 2207/30088; G16H 30/40; G16H 50/20
See application file for complete search history.

(56) References Cited

U.S. PATENT DOCUMENTS

| | | | | |
|---|---|---|---|---|
| 8,260,010 | B2* | 9/2012 | Chhibber | A61B 5/4875 |
| | | | | 382/128 |
| 8,515,144 | B2* | 8/2013 | Kuo | G06T 7/62 |
| | | | | 382/128 |
| 9,089,303 | B2* | 7/2015 | Chen | A61B 5/0059 |

(Continued)

OTHER PUBLICATIONS

Leong et al., "Identification of Skin Conditions with Convolutional Neural Networks: A Deep Learning Approach", 2024 3rd International Conference on Digital Transformation and Applications (ICDXA), Jan. 29-30, 2024, pp. 205-209 (Year: 2024).*

(Continued)

*Primary Examiner* — Ping Y Hsieh
*Assistant Examiner* — Jose M Torres
(74) *Attorney, Agent, or Firm* — Perspectives Law Group, Corp.

(57) ABSTRACT

A method of operation of a compute system includes: qualifying a patient image for analyzing a suspected skin condition; detecting a skin area in the patient image; segmenting the skin area into a segmented image including the suspected skin condition; cropping the segmented image to form a cropped image including the suspected skin condition at a center of the cropped image; analyzing the suspected skin condition to identify a skin disease result and a disease subclass from the cropped image; and assembling a disease identification display including the patient image, a skin disease indication, an image match score, and the disease subclass for displaying on a device.

20 Claims, 15 Drawing Sheets
(12 of 15 Drawing Sheet(s) Filed in Color)

(56) References Cited

U.S. PATENT DOCUMENTS

| | | | |
|---|---|---|---|
| 9,286,537 B2* | 3/2016 | Radha Krishna Rao | ................... G06V 10/42 |
| 9,750,450 B2 | 9/2017 | Shie et al. | |
| 10,182,757 B2* | 1/2019 | Gareau | ................. A61B 5/441 |
| 10,593,040 B2 | 3/2020 | Zouridakis | |
| 10,878,567 B1 | 12/2020 | Abid et al. | |
| 11,640,663 B1* | 5/2023 | Choe | ...................... G06V 10/60 382/128 |
| 2008/0214907 A1* | 9/2008 | Gutkowicz-Krusin | ...................... A61B 5/445 600/306 |
| 2009/0279760 A1* | 11/2009 | Bergman | ................ G06T 7/136 382/128 |
| 2012/0008838 A1* | 1/2012 | Guyon | ................... G16H 50/20 382/128 |
| 2013/0331708 A1* | 12/2013 | Estocado | ............... A61B 5/444 600/477 |
| 2014/0316235 A1 | 10/2014 | Davis et al. | |
| 2015/0025343 A1* | 1/2015 | Gareau | ................ A61B 5/0075 600/328 |
| 2016/0299009 A1* | 10/2016 | Jeon | ...................... G01J 5/0025 |
| 2017/0083793 A1 | 3/2017 | Shie et al. | |
| 2017/0231550 A1* | 8/2017 | Do | ........................ G06T 7/0012 382/128 |
| 2019/0188851 A1 | 6/2019 | Zouridakis | |
| 2020/0302608 A1* | 9/2020 | Kaffenberger | ........... G06N 3/08 |
| 2022/0051409 A1* | 2/2022 | Maclellan | .............. G16H 50/70 |
| 2022/0156932 A1* | 5/2022 | Fujisawa | .............. G16H 30/40 |
| 2023/0210610 A1 | 7/2023 | Roh et al. | |
| 2023/0248998 A1* | 8/2023 | Natarajan | .............. G16H 30/20 600/1 |

OTHER PUBLICATIONS

Son et al., "AI-based localization and classification of skin disease with erythema", Scientific Reports (2021) 11:5350, pp. 1-14 (Year: 2021).*

Varalakshmi et al., "Computer-Aided Design for Skin Disease Identification and Categorization Using Deep Learning", 2023 7th International Conference on Image Information Processing (ICIIP), pp. 1-6 (Year: 2023).*

* cited by examiner

COMPUTE SYSTEM WITH SKIN DISEASE IDENTIFICATION MECHANISM AND METHOD OF OPERATION THEREOF

TECHNICAL FIELD

An embodiment of the present invention relates generally to a compute system, and more particularly to a system with a skin disease identification mechanism.

BACKGROUND

In today's environment, there is an increasing number of skin conditions and diseases that impact our society. The identification and treatment of these skin diseases can be greatly enhanced by early detection. Medical professionals base any diagnosis on their experience and training. It is possible that multiple Doctors can view the same patient and diagnose with different diseases. Providing an accurate diagnosis can change the course of the disease. An incorrect diagnosis can be physically and emotionally devastating.

Thus, a need still remains for a compute system with a skin disease identification mechanism to provide an accurate diagnosis of skin disease to assist healthcare professionals. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: qualifying a patient image for analyzing a suspected skin condition; detecting a skin area in the patient image; segmenting the skin area into a segmented image including the suspected skin condition; cropping the segmented image to form a cropped image including the suspected skin condition at a center of the cropped image; analyzing the suspected skin condition to identify a skin disease result and a disease subclass from the cropped image; and assembling a disease identification display including the patient image, a skin disease indication, an image match score, and the disease subclass for displaying on a device.

An embodiment of the present invention provides a compute system, including a control circuit, including a processor, configured to qualify a patient image to analyze a suspected skin disease; detect a skin area in the patient image; segment the skin area into a segmented image including the suspected skin condition; crop the segmented image to form a cropped image including the suspected skin condition at a center of the cropped image; analyze the suspected skin condition to identify a skin disease result and a disease subclass from the cropped image; and a communication circuit, coupled to the control circuit, configured to assemble a disease identification display including the patient image, a skin disease indication, an image match score, and the disease subclass for displaying on a device.

An embodiment of the present invention provides a non-transitory computer readable medium including instructions for a compute system, including: qualifying a patient image for analyzing a suspected skin condition; detecting a skin area in the patient image; segmenting the skin area into a segmented image including the suspected skin condition; cropping the segmented image to form a cropped image including the suspected skin condition at a center of the cropped image; analyzing the suspected skin condition to identify a skin disease result and a disease subclass from the cropped image; and assembling a disease identification display including the patient image, a skin disease indication, an image match score, and the disease subclass for displaying on a device.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
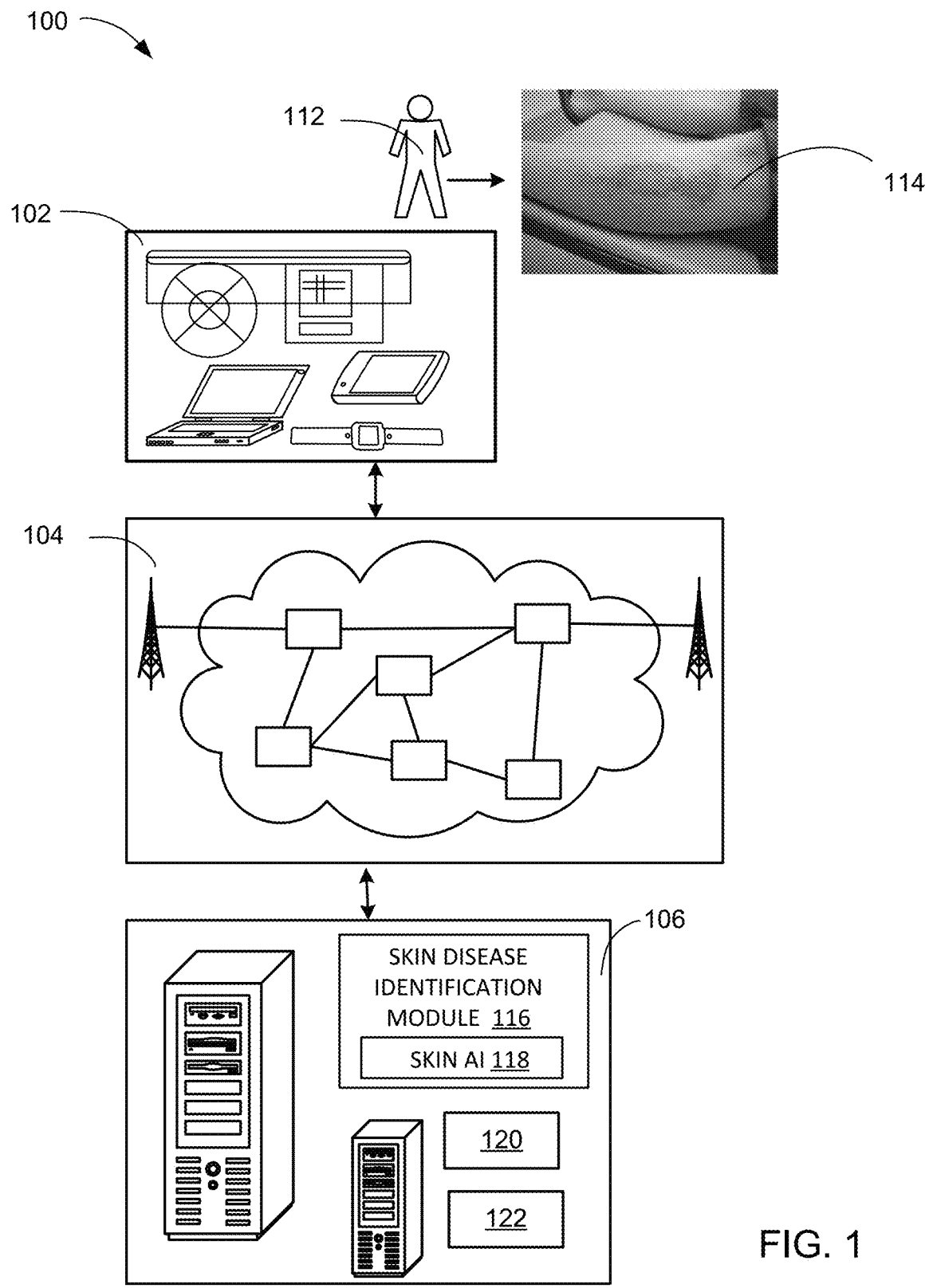
FIG. 1 is an example of a system architecture diagram of a compute system with a skin disease identification mechanism in an embodiment of the present invention.

The skin disease identification mechanism is intended to help the user detect all skin diseases based on clinical skin images. The list of diseases that can be detected contains 1400 skin conditions, divided in to 116 super-classes of diseases, and 40 groups of diseases, including skin tumors, skin infections and infestations, inflammatory skin diseases, genodermatoses, tropical skin diseases, drug reactions, nail diseases, oral diseases, etc. A superclass may belong to one or several groups; for example "Pemphigus Pemphigoid" superclass belongs to "Blistering" and "Autoimmune" groups. This skin disease list contains all the common skin diseases, and also many rare and very rare diseases, such porphyria cutanea tarda, xeroderma pigmentosum, mycetoma, drug-induced flagellate erythema, and so on. The list of diseases may be updated in new releases of the skin disease identification mechanism to include new diseases and improve its logical structure.

The skin disease identification mechanism can provide a suggestion or guidance for professional users, such as a dermatologist, a general doctor, or a clinician,—person who have qualification to make a medical diagnosis) and from that he can study/review/look up for more information about our suggested list and give his own final decision for his patient. So the app's intended users are professorial users and not patients, and its intended use is to give a suggestion/reference and not a diagnosis.

Making a diagnosis through just one image is not an easy task. Sometimes looking at one image/photo does not provide enough information for diagnosis. Doctor may need to see several images by looking at the lesion of his patient from several angles, or asking more information about the symptoms inside the patient's body, or even doing a biopsy test. Besides, there could be more than one disease/skin condition displayed in one image. Some geometric feature could belong to several diseases.

As mentioned above, doctors can miss some skin disease during their annotation process. If an artificial intelligence (AI) model or machine learning (ML) model learn or are trained with those images, the images with the missed annotation will create a confusion and inconsistency (because of non-labeled skin disease, the AI/ML model will learn or be trained that the missed annotated images are not skin disease when those images should be labeled as skin disease).

Embodiments of the compute system with a skin disease identification mechanism provide more consistent and accurate skin disease scoring and classifies different types of skin disease for diagnostics at least by recognizing multiple skin disease in a given image and assessing each while other often miss skin disease locations as well as limit the number of skin disease in a given image. As examples of embodiments, the compute system with the skin disease identification mechanism can identify, segment, or a combination thereof all or multiple skin disease and skin disease-like on a given image. Continuing with the example, the identification and segmentation can be implemented by a segmentation model or module, which will be described more later. Embodiments of the compute system with the skin disease identification mechanism do not need doctors to do this work and avoiding some of the challenges as noted above. Further, embodiments eliminate or reduce the probability of missing skin disease.

Continuing with examples of embodiments, the compute system with the skin disease identification mechanism can perform segmentation, generating more precise results than bounding boxes. Further continuing the examples, the compute system with the skin disease identification mechanism can classify the detected skin disease. The compute system with the skin disease identification mechanism can utilize annotated data from doctors as input as labeled data to training the AI/ML models of the compute system with the skin disease identification mechanism and can compensate for the missing skin disease annotation by the doctors leading to solving inconsistency problem.

The compute system with the skin disease identification mechanism can utilize skin disease identification, skin disease scoring, and skin disease segmentation to compute area of each skin disease, without requiring training for the area calculation of each skin disease. The compute system with the skin disease identification mechanism process through skin disease area calculation for each skin disease provide consistent results for diagnostics. Continuing the examples for embodiments, the compute system with the skin disease identification mechanism generates an image match score from 0 to 1.00, which is precise or objective value while also being sensitive in the changing of number of skin disease and each of its severity. The consistent and accurate scoring as well as the skin disease area computation from the compute system with the skin disease identification mechanism can also be utilized to track the progress of treatment.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof. The word "module" or "model" can be also be used interchangeable depending on the context it is described or used in the written description. The "model" can represent one or more artificial intelligence models, machine learning models, or a combination thereof. The term "skin disease" referred to herein means any type of skin disease including porphyria cutanea tarda, xeroderma pigmentosum, mycetoma, drug-induced flagellate erythema, and the like, without limitation.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below, the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication. It is understood that the modules described in this document can be executed individually or in combination without limitation.

The word "module" or "model" can be also be used interchangeable depending on the context it is described or used in the written description. The "model" can represent one or more artificial intelligence models, machine learning models, or a combination thereof. It is understood the models identified in the description can be operated concurrently, in sequence, or in alternative without changing the operation of the models.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a system architecture diagram of a compute system 100 with a skin disease identification mechanism in an embodiment of the present invention. Embodiments of the compute system 100 provide standardized and objective skin disease scoring for each of the skin disease, as described earlier.

The compute system 100 can include a first device 102, such as a client or a server, connected to a second device 106, such as a client or server. The first device 102 can communicate with the second device 106 through a network 104, such as a wireless or wired network.

For example, the first device 102 can be of any of a variety of computing devices, such as a smart phone, a tablet, a cellular phone, personal digital assistant, a notebook computer, a wearable device, internet of things (IoT) device, or other multi-functional device. Also, for example, the first device 102 can be included in a device or a sub-system.

The first device 102 can couple, either directly or indirectly, to the network 104 to communicate with the second device 106 or can be a stand-alone device. The first device 102 can further be separate form or incorporated with a vehicle, such as a car, truck, bus, motorcycle, or a drone.

For illustrative purposes, the compute system 100 is described with the first device 102 as a mobile device, although it is understood that the first device 102 can be different types of devices. For example, the first device 102 can also be a non-mobile computing device, such as a server, a server farm, cloud computing, or a desktop computer.

The second device 106 can be any of a variety of centralized or decentralized computing devices. For example, the second device 106 can be a computer, grid computing resources, a virtualized computer resource, cloud computing resource, routers, switches, peer-to-peer distributed computing devices, or a combination thereof.

The second device 106 can be centralized in a single room, distributed across different rooms, distributed across different geographical locations, embedded within a telecommunications network. The second device 106 can couple with the network 104 to communicate with the first device 102. The second device 106 can also be a client type device as described for the first device 102.

For illustrative purposes, the compute system 100 is described with the second device 106 as a non-mobile computing device, although it is understood that the second device 106 can be different types of computing devices. For example, the second device 106 can also be a mobile computing device, such as notebook computer, another client device, a wearable device, or a different type of client device.

Also, for illustrative purposes, the compute system 100 is described with the second device 106 as a computing device, although it is understood that the second device 106 can be different types of devices. Also, for illustrative purposes, the compute system 100 is shown with the second device 106 and the first device 102 as endpoints of the network 104, although it is understood that the compute system 100 can include a different partition between the first device 102, the second device 106, and the network 104. For example, the first device 102, the second device 106, or a combination thereof can also function as part of the network 104.

The network 104 can span and represent a variety of networks. For example, the network 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 104. Further, the network 104 can traverse a number of network topologies and distances. For example, the network 104 can include direct connection, personal area network (PAN), local area network (LAN), metropolitan area network (MAN), wide area network (WAN), or a combination thereof.

Returning to the description standardized and objective skin disease scoring of the embodiments of the compute system 100, as an example, the compute system 100 provide functions to various users 112, including patients and clinicians. The compute system 100 can provide functions to the users 112 in a number of ways.

For example, the compute system 100 can provide the functions for the users 112 with the first device 102, the second device 106, distributed between these two devices, or a combination thereof. Also, as examples, the compute system 100 can provide a mobile application for the patients, the clinicians, or a combination thereof. Further as an example, the compute system 100 can provide the functions via a web-browser based applications or a software to be executed on the first device 102, the second device 106, distributed between these two devices, or a combination thereof.

In one embodiment as an example, patient images 114 are taken and uploaded by the patient and reviewed by the clinician. In this embodiment, a patient or the clinician launches the skin disease identification mechanism via the mobile application and logs into the patient's account. The patient can be prompted to upload or take body images as the patient images 114. The compute system 100 can guide a patient on photo guidelines for the patient images 114 and accepts or rejects the patient images 114 for retake based on a pre-specified criteria, e.g., distance, quality, blur, luminosity, or a combination thereof. The compute system 100 can also provide guides for a patient on capturing videos as opposed to still photos. The patient images 114 can be selected from the video.

Once the patient images 114, as required for analysis, are successfully uploaded, the compute system 100 can send or load the patient images 114 to the skin disease identification module 116 for analysis including a skin disease artificial intelligence (AI) 118. The skin disease identification module 116 will be described later. For brevity and clarity and as an example, the skin disease identification module 116 is shown in FIG. 1 as being executed in the second device 106 although it is understood that portions can operate on the first device 102, such as the mobile app or the web-browser based application, can operate completely on the first device 102, or a combination thereof. As a further example, the skin disease identification module 116 can be implemented in software running on specialized hardware, full hardware, or a combination thereof.

The skin disease AI 118 can be software executed on a processor, core, ASIC, specialized GPU, or a combination thereof configured as a machine learning structure. The combination of hardware decision nodes including for example gates and switches combined with a machine learning software that can process the patient images 114 at a pixel level.

Based on analysis results, the compute system 100 can display information to the patient including a recommendation based on the patient images 114, uploaded, for the patient to schedule a visit with your primary care physician or with a specialist based on a skin disease indication 120, which may or may not be visible or recognized by to the patient.

If the skin disease identification module 116 provides the skin disease indication 120 below an image match score 122, the compute system 100 can display a message that based on the patient images 114, uploaded, the patient may not need a visit with your primary care physician or with other specialists. The compute system 100 can provide a function allowing the patient to schedule a visit with the clinician.

Continuing the example, the compute system 100 can provide a function that allows the clinician to access the patient images 114 uploaded by the patient and the skin disease indication 120, such as the skin disease image match score, the skin disease area, or a combination thereof through the web-based dashboard from the skin disease diagnostic mechanism. The compute system 100 allows the clinician to make edits to annotations determined by the skin disease identification module 116 and the scores (if necessary) and saves the results. The clinician can utilize the skin disease indication 120 to make the diagnostic decision and provide necessary treatment steps (if applicable).

In a further embodiment as an example, the compute system 100 can allow a patient to schedule a visit with a primary care physician or with a specialist. A clinician can launch the skin disease identification mechanism, such as a mobile application and log in. The compute system 100 can be prompted to upload or take the patient images 114 of the patient's body or body parts to be analyzed by the skin disease identification module 116.

The compute system 100 can provide guidance to the clinician on the photo guidelines. The compute system 100 can accept or reject images for retake based on a pre-specified criteria, such as distance, quality, blur, luminosity, or a combination thereof. Once the patient images 114 are successfully uploaded, the compute system 100 and send or load the patient images 114 to the skin disease identification module 116 for analysis.

Continuing the example, the compute system 100 can similarly provide a function that allow the clinician to access the patient images 114 uploaded by the patient and the skin disease indication 120, such as with the web-based dashboard from the skin disease identification mechanism. The compute system 100 allows the clinician to make edits to annotations determined by the skin disease identification module 116 and the scores (if necessary) and saves the results. The clinician can utilize the skin disease indication 120 to make the diagnostic decision and provide necessary treatment steps (if applicable).

Figure 2:
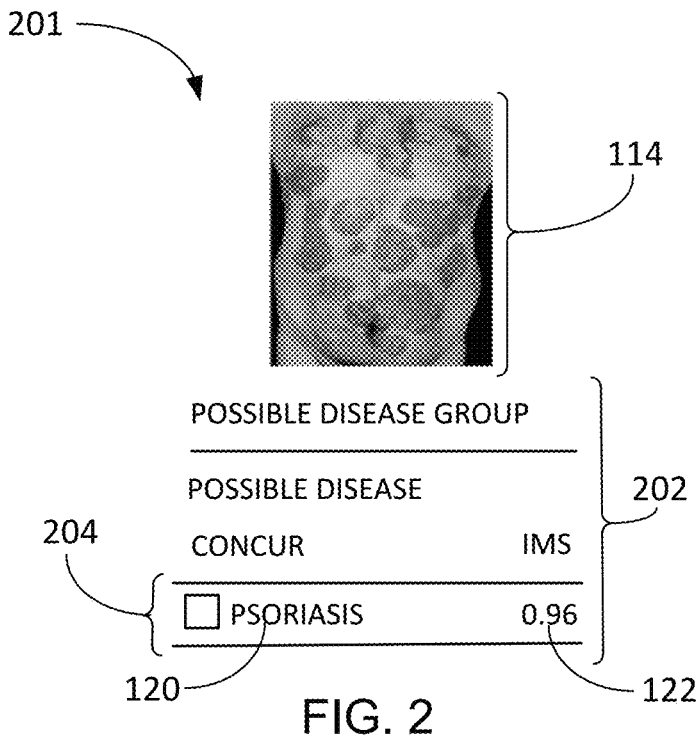
FIG. 2 is an example of a disease identification display from an input image in an embodiment.

Referring now to FIG. 2, therein is shown an example of a disease identification display 201 from an input image 114 in an embodiment. The compute system 100 of FIG. 1, the skin disease identification module 116 of FIG. 1, or a combination thereof can process the patient images 114. The disease identification display 201 is an example of an output of the skin disease identification module 116.

The disease identification display 201 can include the patient image 114 and a skin disease identification report 202. The skin disease identification report 202 can include a skin disease result 204. The skin disease result 204 can include the skin disease indication 120 and the image match score 122. It is understood that the skin disease identification report 202 can include multiple versions of the skin disease result 204 indicating different ones of the skin disease indication 120 and the image match score 122 representing multiple classes of the skin disease identified in the patient image 114.

Figure 3:
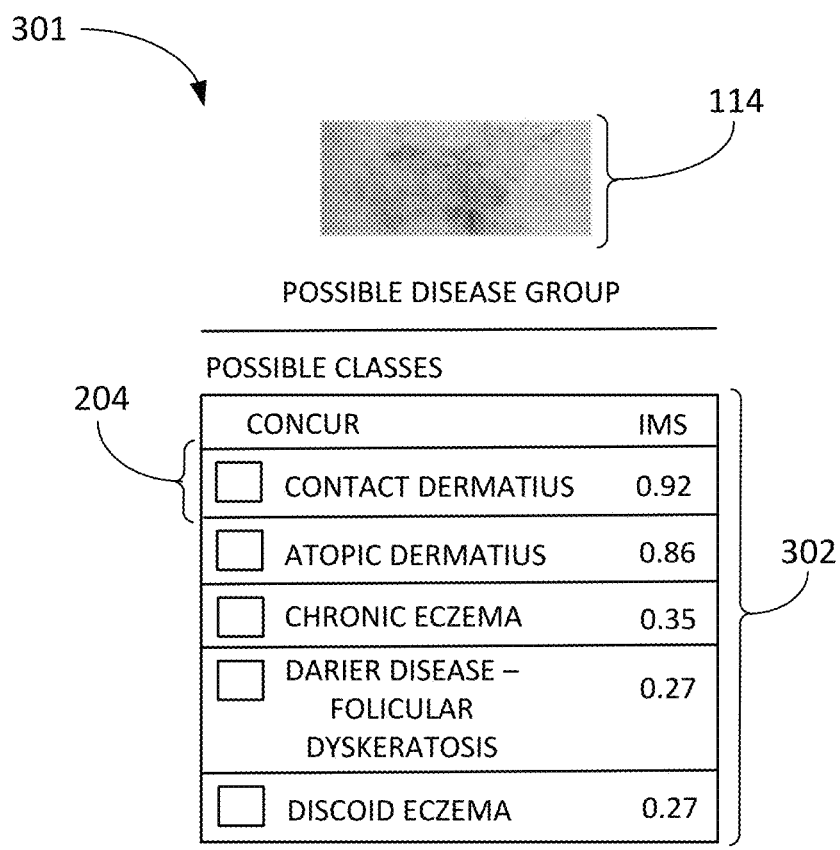
FIG. 3 is an example of a disease identification display from an input image in a further embodiment.

Referring now to FIG. 3, therein is shown an example of a disease identification display 301 from an input image 114 in a further embodiment. An example of the disease identification display 301 in an embodiment can be displayed on the first device 102, the second device 106, or a combination thereof. FIG. 3 is as an example of the disease identification display 301 of an output of the compute system 100 of FIG. 1, the skin disease identification module 116 of FIG. 1, or a combination thereof to be displayed to the user 112 of FIG. 1.

In this example, the patient image 114 is shown with the skin disease result 204. In this example, the input is a body part image as the patient image 114 to the compute system 100, the skin disease identification module 116, or a combination thereof. The output is shown in the disease identification display 301 including a skin disease identification list 302 of each type of the skin disease indication 120 and the image match score 122 provided with the most significant of the image match score 122 listed at the top of the skin disease identification list 302.

It is understood that the disease identification display 301 can be transmitted to the user 112 of FIG. 1 to provide analysis of the user's skin disease of the items listed in the skin disease identification list 302. The disease identification display 301 can be used to monitor changes in the skin disease identification list 302 over time.

Figure 4:
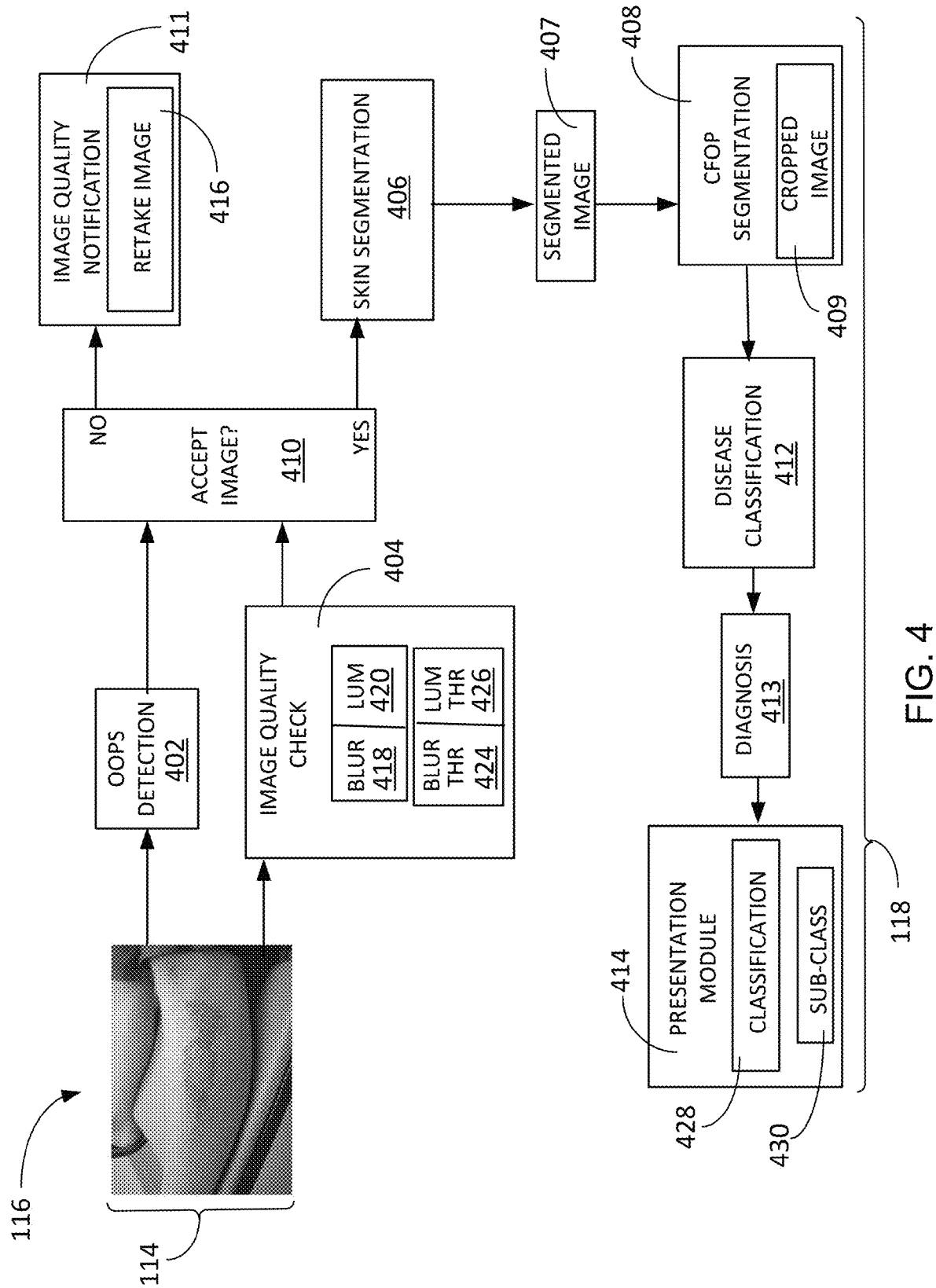
FIG. 4 is an example of a control flow of the compute system with the skin disease identification mechanism in an embodiment.

Referring now to FIG. 4, therein is shown an example of a block diagram of the compute system 100 with the skin disease identification module 116 in an embodiment. In the example depicted in FIG. 4, the processing of the patient image 114 can be depicted at least as shown in FIG. 2 with skin disease report 202 and skin disease result 204 and can be performed by the compute system 100 of FIG. 1, the skin disease identification module 116 of FIG. 1, or a combination thereof.

In this example, the patient image 114 is processed with an Oops detection module 402 to detect whether if the patient image 114 is skin related or not. The flow can concurrently submit the patient image 114 to an Image quality check module 404 to verify if the quality of the patient image 114 is sufficiently detailed for analysis by the skin disease identification module 116 utilizing the Skin disease AI 118 of FIG. 1.

In this example, the block diagram can couple the oops detection module 402 and the image quality check module 404 to an acceptable image module 410 to complete the analysis of the patient image 114. Continuing the example, the image quality check module 404 can function as a filter for preventing poor quality images from being used as input for a skin disease classification module 412. Poor quality images refer to images that are too blurry or images that are of too bad luminosity (either too bright, too dark or too noisy). Eventually, the image quality check module 404 is a classification module whose possible output classes are acceptable or unacceptable.

The oops detection module 402 and the image quality check module 404 can be coupled to the acceptable image module 410. The acceptable image module 410 can be a hardware structure that accepts the output of the oops detection module 402 and the image quality check module 404 to determine whether the instance of the patient image 114 is acceptable for analysis. The oops detection module 402 can verify that at lease 20% of the area of the patient image 114 includes skin in order to be considered relevant. If the patient image 114 includes less that 20% of the area covered by skin, the patient image 114 is considered irrelevant.

The acceptable image module 410 can prioritize the output of the oops detection module 402 during the analysis process. By way of an example, if the oops detection module 402 declares the patient image 114 to be irrelevant, the NO output will be activated to alert an image quality notification module 411 that the patient image 114 is unacceptable and must be replaced by a better version of the patient image 114. The image quality notification module 411 can generate a retake image message 416 indicating insufficient skin area shown, please retake the image.

If the acceptable image module 410 receives an indication that the patient image 114 is relevant, it looks to the output of the image quality check module 404 to determine the acceptability of the patient image 114. The image quality check module 404 can identify a blurry image, a distant image, an image with bad luminosity (either too dark or too bright), or a combination thereof. The image quality check module 404 can reject the patient image 114 as being the blurry image, the distant image, or the image with bad luminosity, which will activate the NO output of the acceptable image module 410. In this case the retake image message 416 will indicate the patient image 114 is the blurry image, the distant image, or the image with bad luminosity and must be retaken in order to proceed with the analysis.

When the acceptable image module 410 identifies the output of the oops detection module 402 as a relevant image and the output of the image quality check module 404 indicates the patient image 114 is acceptable, the YES output is activated and a skin segmentation module 406 can accept the patient image 114 for analysis. It is understood that the interface between the acceptable image module 410 and the image quality notification module 411 provides sufficient information to generate an appropriate version of the retake image message 416.

The skin segmentation module 406 including a skin module 406, a skin detection module 406, or a combination thereof can process the patient image 114 through the rest of the skin disease identification module 116. The image quality check module 404 can be implemented in a number of ways.

As specific examples, the image quality check module 404 provides quality criteria including a blurry metric 418, a bad luminosity metric 420, or a combination thereof. Further as a specific example, the quality criteria can be a two-dimensional vector with the blurry metric 418, and the bad luminosity metric 420.

The blurry metric 418 is used to measure the how clear or blurry the patient image 114 being processed is. The value for the blurry metric 418 is set for the patient image 114 used for training the image quality check module 404 of what is considered clear and what is consider not clear or blurry. If the value of the blurry metric 418 indicates that the patient image 114 is not clear or blurry, then the skin disease identification module 116 or portions thereof cannot analyze the instance of the patient images 114 to compute the skin disease indication 120. If the value of the blurry metric 418 indicates that the image is clear or not blurry, then the skin disease identification module 116 or portions thereof can analyze the instance of the patient images 114 to compute the skin disease indication 120.

The bad luminosity metric 420 is used to measure the lighting or brightness or dimness of the patient image 114 being processed. The value for bad luminosity metric 420 is set for the patient image 114 used for training the image quality check module 404 of what is considered too dim and what is consider not dim. If the value of the bad luminosity metric 420 indicates that the image is dim, then the skin disease identification module 116 or portions thereof cannot analyze the instance of the patient images 114 to compute the skin disease indication 120. If the value of the bad luminosity metric 420 indicates that the image is not too dim, then the skin disease identification module 116 or portions thereof can analyze the instance of the patient images 114 to compute the skin disease indication 120.

The metrics of the quality criteria can be measured with a blurry threshold 424 and a luminosity threshold 426 collectively, as subsets, as equal priority, or of non-equal priority. The term equal priority refers to all the metrics are compared with equal weight to segregate the image match score 122 for the patient image 114 to be deemed acceptable and continue to be processed by the skin disease identification module 116. The term non-equal priority refers to the varying weight of the metrics relative to each other where some can have more importance over the other metrics. As an example, one of the metrics of the quality criteria alone can be used to determine if the patient image 114 is acceptable or not for the image to continue to be processed by the skin disease identification module 116.

As a specific example, if an instance of the patient images 114 is relevant or usable to compute the skin disease indication 120 by the skin disease identification module 116, then the acceptable image module 410 can determine that instance of the patient images 114 continues processing to the skin segmentation module 406. In this example, the image quality check module 404 checks each of the instance of the patient images 114 and outputs a two-dimensional vector for the scores for the blurry metric 418, and the bad luminosity metric 420. The value for the bad luminosity metric 420 can also represent the noise in the patient image 114 being processed.

Continuing with the specific example, the sum of output vector for the quality criteria does not need to be 1. There can be two high values at the same time: [99.6, 98.0] for the blurry metric 418, and the bad luminosity 420, respectively, which means the input image can be blurry or not clear and in bad light quality.

The blurry metric 418 and the bad luminosity metric 429 are compared to the blurry threshold 424 and the bad luminosity threshold 426, respectively. The value of the blurry metric 418 that is greater than the blurry threshold 424 can reject the patient image 114 as unacceptable and the bad luminosity metric 420 that is greater than the bad luminosity threshold 426 can reject the patient image 114 as unacceptable.

In other words, as an example, if the values for the blurry metric 418 and the bad luminosity metric 420 indicates bad light condition are lower than the blurry threshold 424 and the bad luminosity threshold 426, respectively, then the image quality check module 404, accepts the input image or the instance of the patient images 114 being processed at the time. Otherwise, the input image or the instance of the patient images 114 being processed at the time will be classified into blurry if the value for the blurry metric 418 is higher than the value for the bad luminosity metric 420 and vice versa. Further, the metric (blurry metric 418 or the bad luminosity metric 420) with the larger value can be used to provide feedback to improve performance of the compute system 100 if the image quality check module 404 rejects the image.

Continuing the example, the patient images 114 that are processed and determined by the image quality check module 404 to continue processing by the compute system 100, the skin disease identification module 116, or a combination thereof, the flow can proceed from the acceptable image module 410 to the skin segmentation module 406. The skin segmentation module 406 can segment skin region included eyes, nails, tattoo on skin, sick skin (for example psoriasis, skin tumors, etc.). The skin segmentation does not optionally segment scalp unless the scalp is visible (i.e., there are not too much hair covering it). The skin segmentation module 406 can ignore the object on skin such as clothes, bracelet, etc. However, the skin segmentation module 406 can still segment the visible skin like skin under transparent objects, such as glasses to produce a segmented image 407. It is understood that the segmented image 407 comprises the patient image 114 with all non-skin regions of the image blacked out to remove non necessary background noise.

Continuing with the example, the compute system 100, the skin disease identification module 116, or a combination thereof can detect skin and blackout all non-skin region of the patient image 114 with the skin segmentation module 406. The flow can continue to a crop segmentation module 408 to segment the suspected skin disease and skin disease-like area of the segmented image 407. Based on the result of the crop segmentation module 408, the compute system 100, the skin disease identification module 116, or a combination thereof can receive a cropped image 409, having any unnecessary background removed from the segmented image 407, with any suspected skin disease-like area in the center.

The compute system 100, the skin disease identification module 116, or a combination thereof can score the cropped images using Skin disease classification module 412. The skin disease AI 118 can include the oops detection module 402, the image quality check module 404, the skin segmentation module 406, the crop segmentation module 408, the skin disease classification module 412, and a presentation module 414 for identifying and classifying the skin disease classification 428 and a skin disease sub-class 430. The Skin disease classification module 412 can identify each of the skin disease diagnosis 413 identified in the patient image 114. The Skin disease classification module 412 generates a score from 0 to 5 for each cropped image. The higher score, the more severe it is. Using the skin segmentation module 406, the crop segmentation module 408, and the Skin disease classification module 412, the compute system 100, the skin disease identification module 116, or a combination thereof can compute the image matching score 122 of FIG. 1 in the presentation module 414 to generate the final order for each of the skin disease result 204 of FIG. 2 in the skin disease identification list 302 of FIG. 3.

The compute system 100, the skin disease identification module 116, or a combination thereof can be trained each module individually. Once every single module performs well (that is the obtained metrics are greater or higher than some good threshold depending on each module. For example, the skin segmentation has to have similarity coefficient, such as a Jaccard score, higher than 0.8), the compute system 100, the skin disease identification module 116, or a combination thereof can be trained, tested, or a combination thereof as the whole system together. In this training process, a test set is not part of the training set. The test set can include a variety of data for example different skin tone, different parts of the face or body, different resolution, etc. Every time, if any portion of the compute system 100, the skin disease identification module 116, or a combination thereof can provide an update, which can be from one module, from one algorithm, the compute system 100, the skin disease identification module 116, or a combination thereof can predict skin disease on those images by running through the skin disease identification module 116. After the raw results, the compute system 100, the skin disease identification module 116, or a combination thereof can run statistical tests and compare the analysis result with the one of an older version. If the result is better, the compute system 100, the skin disease identification module 116, or a combination thereof can keep the update.

The metric to measure accuracy of the model is mean absolute error (MAE) that is a measure of errors between paired observations expressing the same phenomenon. MAE is calculated as the sum of absolute errors divided by the sample size. And the Mean absolute error (MAE) is computed as:

$$MAE = \frac{1}{n}\sum_{i=1}^{n}|Y_i - \hat{Y}_i| \quad (2.2)$$

These functions can quantify the errors made by the module: the lower their value is, the better it is for the module. They can also be considered as distances between true and predicted values, L1-distance for the MAE, and L2-distance for the MSE. They are mostly used in regression problems, where the output is a real number.

This means that the compute system 100, the skin disease identification module 116, or a combination thereof can utilize this function as a loss function during the training of a regression problem. On the other side, MAE, which has not this easy optimization property due to the absolute value in its definition, is useful for measuring how far from the true values are predicted values. Indeed, this function gives values in the same scale and unit as the predicted values, which allow more interpretation and understanding for human eyes. Then MAE is often used as a metric during training, to ensure that the module performs well.

Regarding Jaccard score, the Jaccard index, also known as the Jaccard similarity coefficient, is a statistic used for gauging the similarity and diversity of sample sets. It measures the similarity between finite sample sets, it is defined as the ratio of the intersection over the union of the two sets.

$$J(A, B) = \frac{|A \cap B|}{|A \cup B|} \quad (2.4)$$

Regarding intra-class correlation coefficient (ICC), the intra-class correlation coefficient (ICC) is a number, usually found to have a value between 0 and 1. It refers to correlations within a class of data (for example correlations within repeated measurements of weight), rather than to correlations between two different classes of data (for example the correlation between weight and length). Let the variable of observation is defined as:

$$X_{ij}=\mu+a_i+c_{ij} \quad (25)$$

Where a is the group effects and e is the residual effects which are independently normally distributed with mean 0 and $$E(X_{ij})=\mu \text{ and } Var(a_i)=\sigma_a^2; Var(e_{ij})=\sigma_c^2 \quad (26)$$

Then the ICC is defined as $$ICC = \frac{\sigma_a^2}{\sigma_a^2 + \sigma_e^2} \quad (2.7)$$

The binary accuracy is defined as the ratio between number of correct predictions over the total number of predictions. For example, let the ground truth is [1, 1, 0, 1, 0, 0] and the prediction is [0, 1, 1, 0, 1, 0], then the number of correct predictions is 2 (the second position and the last position) and the total number of predictions is 6. So, the Binary accuracy in this case is 2/6=1/3. When the compute system 100, the skin disease identification module 116, or a combination thereof compute Binary accuracy for one image, each pixel of that image is considered as an information valued either 0 or 1. The compute system 100, the skin disease identification module 116, or a combination thereof can compare the predicted values with the ground truth pixel by pixel and get the Binary accuracy as the above formula.

For example, let the ground truth segmented image 407 (3×5 pixels) A and the prediction B be $$A = \begin{bmatrix} 1 & 0 & 0 & 0 & 0 \\ 0 & 0 & 0 & 0 & 0 \\ 0 & 0 & 0 & 0 & 0 \end{bmatrix}; \text{ and } B = \begin{bmatrix} 0 & 1 & 0 & 0 & 0 \\ 0 & 0 & 0 & 0 & 0 \\ 0 & 0 & 0 & 0 & 0 \end{bmatrix} \quad (2.8)$$

Binary accuracy of this example is 0.8 (there are 12 corrected prediction pixels over 15 pixels). However, Jaccard index in this case is 0 since there is only one annotated pixel which is not matched by the prediction.

The Oops detection module 402 can acts as a filter, preventing irrelevant images to be analyzed in parallel with the image quality check module 404. An irrelevant image refers to images that do not contain human skin or has more than 80% background. Eventually, the Oops detection module 402 is a regression module whose output gets a value between 0 and 1 in which a value close to 1 means probably irrelevant and vice versa. The compute system 100, the skin disease identification module 116, or a combination thereof can include a threshold equal to 0.8 to separate the region of irrelevant and relevant, i.e., if output is greater than 0.8, the input is irrelevant, otherwise it is relevant.

As an example, the ImageNet dataset contains 310K images in which there are 34K irrelevant images and the remaining are relevant images. The dataset includes a variety of images of animals, plants, foods and people. It also includes images with very sick skin to normal skin in wide range of skin tone from white to darker skin.

The Oops detection module 402 not only filters irrelevant images, but also to eliminate an image taken from too far distance which makes the human skin part cover less than 20% area. To be able to detect the case, the compute system 100 includes a set of data in which there are images containing human skin covering less than 20% area. The dataset is supplemented with data augmentation creating a set of 94K synthetic images in which a relevant image is merged with an irrelevant one to get a synthetic image in which the background of the relevant image is expanded.

The skin segmentation module 406 can be implemented in a number of ways. As an example, the implementation can be U-net architecture, which includes of an encoder-decoder scheme. The encoder reduces the spatial dimensions in every layer and increases the channels. The decoder increases the spatial dims while reducing the channels. As a specific example, EfficientNet architecture, which is a convolutional neural network architecture and scaling method that uniformly scales all dimensions of depth/width/resolution using a compound coefficient, can be an implementation for the classification and pre-trained on ImageNet dataset for the encoding.

Continuing with the example, the process can continue from the skin segmentation module 406 to the crop segmentation module 408. As an example, the crop segmentation module 408 does not just segment the skin disease but it also segments the skin disease-like marks, for example skin disease scar or mole. The crop segmentation module 408 performs an object detection where compute system 100, the skin disease identification module 116, or a combination thereof can detect every the skin disease diagnosis 413, such as irritated regions of the skin at or near the surface even of very small size. These are challenging problems because machine can get high accuracy without detecting anything. For example, if there are only 5% of skin area having skin disease, the machine will get 95% accuracy when it detects no skin disease and the skin disease pimples 409 do not often have well-defined borders which makes the skin disease segmentation task even more difficult. As a result, different doctors may segment the skin disease diagnosis 413 differently. Therefore, it is very hard to make the machine learn the correct skin disease diagnosis 413. The compute system 100, the skin disease identification module 116, or a combination thereof addresses these challenging problems at least through the selection of the architecture and training dataset.

Continuing with the example, the process can continue from the crop segmentation module 408 to the skin disease classification module 412, or a combination thereof.

The skin disease classification module 412 can be trained in a number of ways with various datasets. For example, the skin disease classification module 412 can be trained with 128×128 pixels images. The training images are cut based on the crop segmentation module 408. That is, after detecting the skin disease spots, the skin disease classification module 412 identifies the center point of each skin disease and let it be the center of 128×128 pixels image. In the input image, there can be many of the skin disease diagnosis 413. The skin disease classification module 412 focuses on the skin disease at the center of the image and classify it, but do not classify the ones not in the center. For example, the skin disease classification module 412 utilizes region of interest (ROI) technique to focus on the chosen skin disease in the patient image 114. That is the inputs of skin disease classification module 412 are one RGB image and one ROI image. As a specific example, the skin disease classification module 412 can be based on an Xception structure, which is a deep convolutional neural network architecture, with a residual layer and multiplication step between original image and ROI.

The skin disease separation module 410 improves the performance of the skin disease classification module 412 can output the skin disease diagnosis 413 that is right next to another of the skin disease diagnosis 413 as one. The erroneous segmentation input to the skin disease classification module 412 results in an incorrect classification either because the two of the skin disease diagnosis 413 are of different types or the skin disease classification module 412 will see two of the skin disease diagnosis 413 as one hence the area or the size will be bigger. All of this sequence can produce an incorrect prediction. The target pixel array 411 can be the smallest pixel array suitable for analysis of the cropped image 409.

The flow can progress with one or more of the following leading to the presentation module 414. As an example, the presentation module 414 can process inputs from the skin segmentation module 406, the crop segmentation module 408, the skin disease classification module 412, or a combination thereof. The compute system 100, the skin disease identification module 116, display module 414, or a combination thereof can return the skin disease result 204. To do that, the result from Skin disease classification module 412, The crop segmentation module 408, and the Skin segmentation module 406 can be compiled to form the skin disease indication 120.

By way of an example, the Skin segmentation module 406 can provide the segmented image 407, the crop segmentation module 408 can provide the region of interest (ROI) having evidence of skin disease in the segmented image 407, and the Skin disease classification module 412 can provide classifying the skin disease classification 428 and a skin disease sub-class 430. The compilation of the outputs of the Skin disease classification module 412, the crop segmentation module 408, and the Skin segmentation module 406 can form the skin disease indication 120.

The functional units or circuits in the first device 102 can work individually and independently of the other functional units or circuits. The first device 102 can work individually and independently from the network 104, the second device 106, other devices or vehicles, or a combination thereof.

The functional units or circuits described above can be implemented in hardware. For example, one or more of the functional units or circuits can be implemented using a gate, circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

Figure 5:
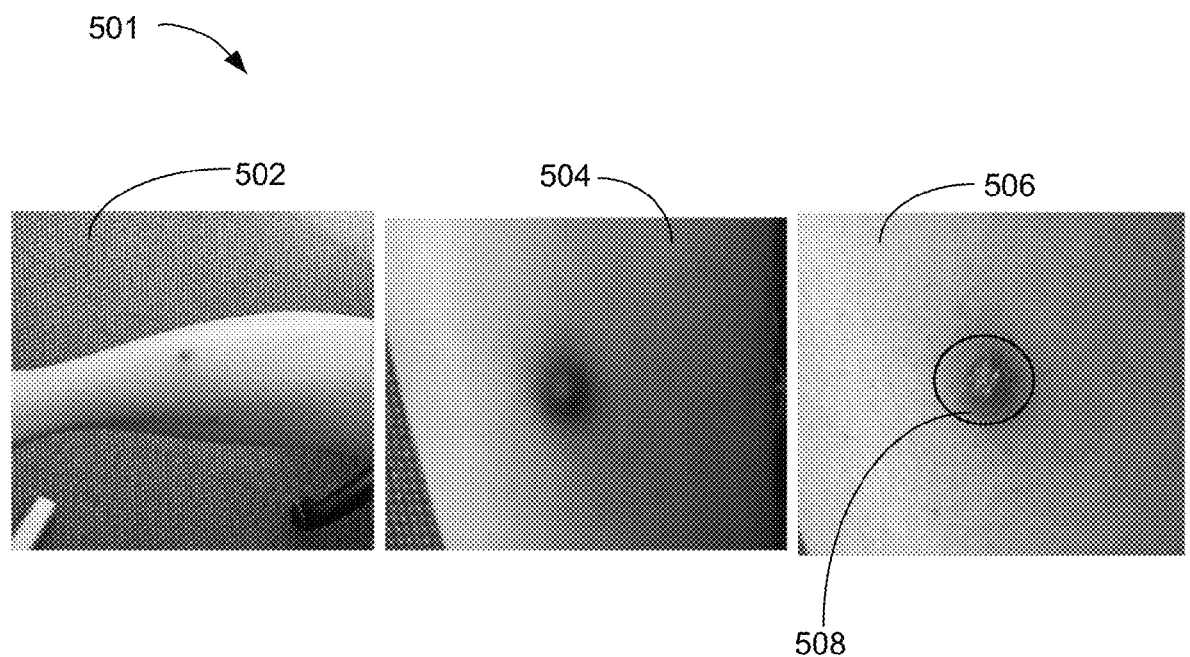
FIG. 5 is an example of a sequence of the input image for evaluation by the image quality check module in an embodiment.

Referring now to FIG. 5, therein is shown an example of a sequence 501 of the input image for evaluation by the image quality check module 404 of FIG. 4 in an embodiment. The sequence 501 includes a distant image 502, a blurry image 504, and an acceptable image 506. The image quality check module 404 can alert the acceptable image module 410 that the distant image 502 and the blurry image 504 are not acceptable and the patient image 114 must be retaken for resubmittal. The acceptable image 506 is verified to be not blurry, not too distant, and must have a correct value of luminosity. By way of an example, the acceptable image 506 can be the cropped image 409 including at least a portion of the suspected skin disease located substantially at a geometric center 508 of the acceptable image 506. The geometric center 508 can be defined as a circular region centered at the intersection of diagonal lines connecting opposite (diagonal) corners of the acceptable image 506.

Figure 6:
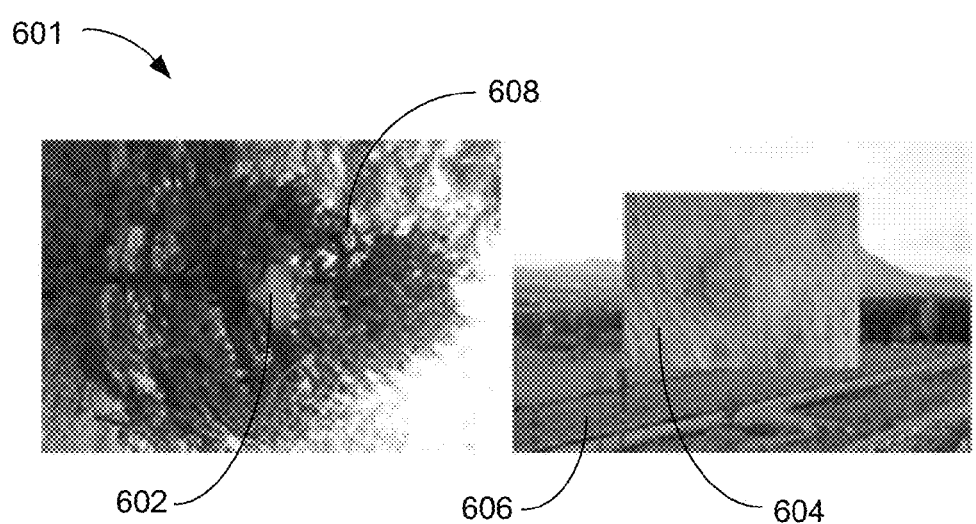
FIG. 6 is an example of synthetic images from input synthesis in an embodiment.

Referring now to FIG. 6, therein is shown an example of synthetic images 601 from input synthesis in an embodiment. The examples depicted in FIG. 6, a skin area 602 and a larger skin area 604 is placed on top of an image of landscape 606 or trees 608. The ImageNet dataset contains 94K synthetic images discussed in FIG. 4 including 81K images that human skin cover from 2% to 18% (called synthetic type 1) and 13K images that human skin cover more than 20% (called synthetic type 2). The dataset labeled synthetic images 601 type 1 as 0.5 and synthetic images type 2 as 0.0. Examples of the synthetic images 601 are used to train the skin disease detection mechanism 116 of FIG. 4.

The training set includes data augmentation with random cropping, making boarder constant, resizing, random rotating, random flipping such that compute system 100, the skin disease identification module 116, or a combination thereof produce output of size 384×384. For validation set, the compute system 100, the skin disease identification module 116, or a combination thereof simply resize images to 384×384 which is the size of the machine learning algorithm's input.

Figure 7:
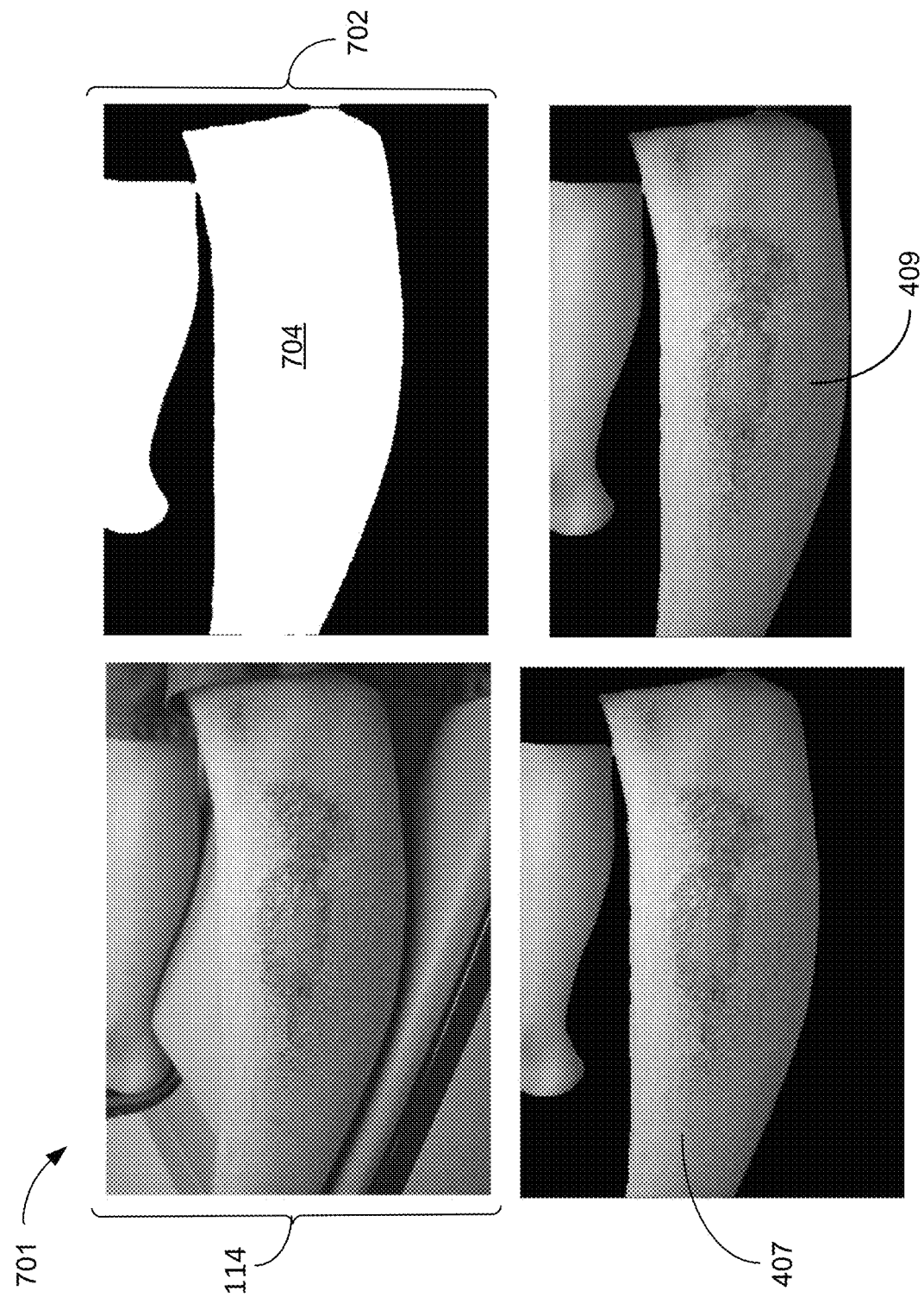
FIG. 7 is an example of a process sequence of the input image as processed by the Skin segmentation module to produce the cropped image in an embodiment.

Referring now to FIG. 7, therein is shown an example sequence 701 of the patient image 114 as processed by the Skin segmentation module 406 of FIG. 4 to produce the cropped image 409 in an embodiment. The patient image 114 can be submitted to the Skin segmentation module 406. The Skin segmentation module 406 can produce an augmented image 702 that can mask all portions that are outside a skin area 704. The Skin segmentation module 406 can then combine the patient image 114 and the augmented image 702 to produce the segmented image 407. The Skin segmentation module 406 can pass the segmented image 407 to the crop segmentation module 408 of FIG. 4 to crop the segmented image 407 to produce the cropped image 409.

Figure 8:
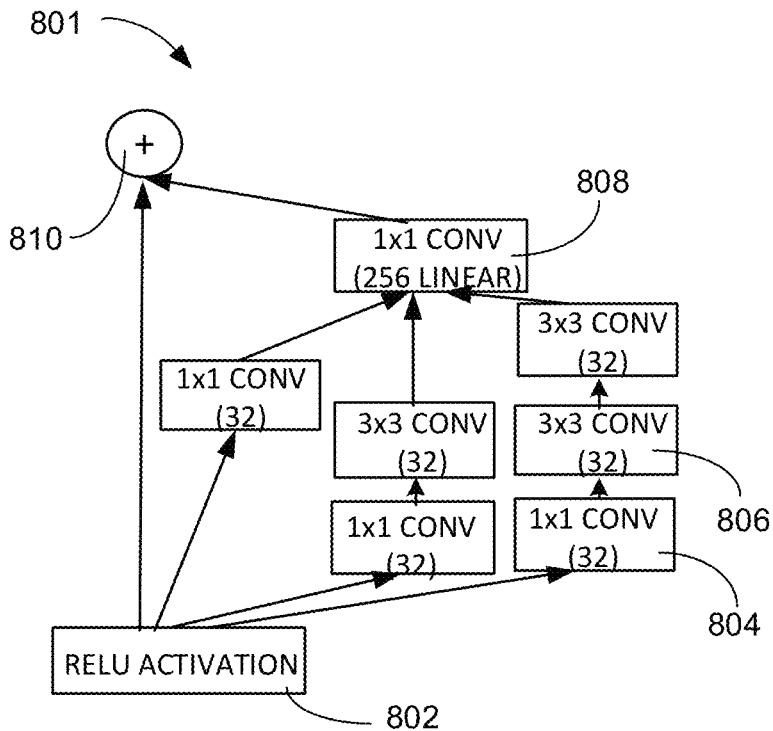
FIG. 8 is an example of a block diagram for an inception module of oops detection module in an embodiment

Referring now to FIG. 8, therein is shown an example of a block diagram 801 for an inception module of oops detection module in an embodiment. The compute system 100, the acne diagnostic module 116, or a combination thereof can be implemented in a number of ways for the oops detection module 402 of FIG. 4. For example, the oops detection module 402 can be implemented with an Inception-ResNet-v2, which is a convolutional neural network that is trained on more than a million images from the ImageNet database, for the encoding part. The Inception-ResNet-v2 is a convolutional neural architecture that builds on the Inception family of architectures but incorporates residual connections (replacing the filter concatenation stage of the Inception architecture).

The convolutional neural network used in the Oops detection module 402 replaces the filter concatenation stage of the Inception architecture with the circuit of FIG. 8 to incorporate residual connections that would otherwise be lost. A relu activation module 802 receives the patient image 114 for processing. The image is dispersed to a series of a detail level converter 804, such as a 1×1 converter in a 32 segment array. The detail level converters 804 can be coupled to a broad area converter 806, such as a 3×3 converter in a 32 segment array. The patient image 114 is submitted to three channels for analysis. The first channel consists of only one of the detail level converter 804. The second channel consists of one of the detail level converter 804 coupled to one of the broad area converter 806. The third channel consists of one of the detail level converter 804 coupled to one of the broad area converter 806 coupled to a second one of the broad area converter 806. A detailed area converter 808, such as a 1×1 converter in a 256 bit linear configuration receives input from the first channel, the second channel, and the third channel in order to provide detailed analysis over the entire input of the patient image 114. A summing node 810 receives the input image of the patient image 114 and the output of the detailed area converter 808 in order to identify skin in the patient image 114.

Figure 9:
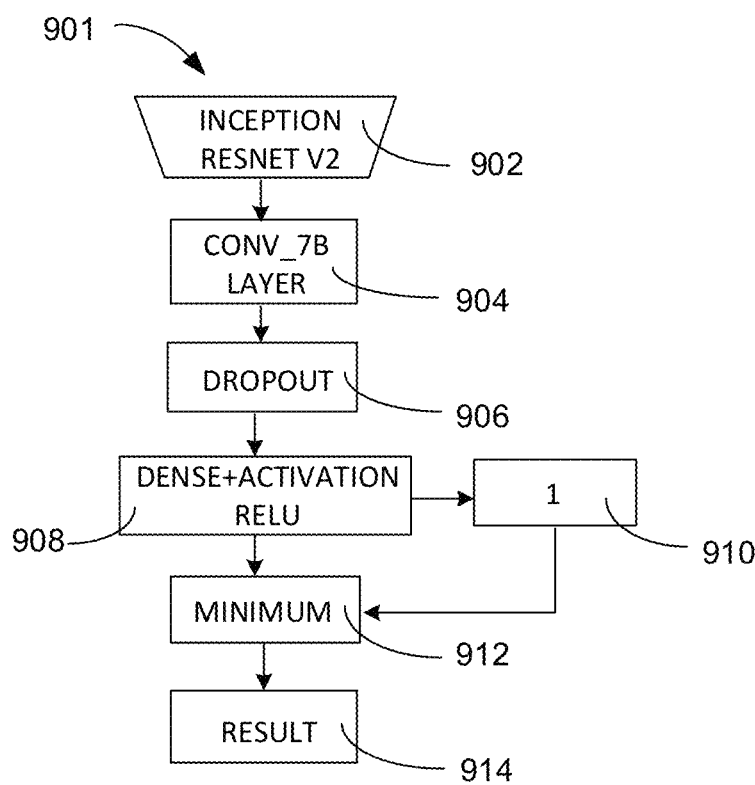
FIG. 9 is an example of a block diagram for another portion of the oops detection module in an embodiment.

Referring now to FIG. 9, therein is shown an example of a block diagram for another portion 901 of the oops detection module 402 of FIG. 4 in an embodiment. Given the patient image 114, the oops detection module 402 can be implemented with a convolutional neural network (CNN) architecture that can return one output as illustrated in FIG. 9. Compared with another encoding, Inception-ResNet-v2 902 gives us robust performance. The Oops detection module 402 contains 783 layers with about 54.3 million parameters.

A Conv_7B Layer module 904 receives the patient image 114 processed by the Inception-ResNet-v2 902 and identifies non-skin areas in the patient image 114. The Conv_7B Layer module 904 is coupled to a dropout module 906. The dropout module 906 can mask out the non-skin areas of the patient image 114. The dropout module 906 is coupled to a dense+activation relu module 908 that can identify skin disease within the skin area 704 of FIG. 7 of the patient image 114 that has not been marked out. The dense+activation relu module 908 is coupled to a loss module 910 and a minimum module 912. The loss module 910 calculates the error interpretation of the analysis of the skin area 704 and identifies a mean absolute error for the calculations of the image match score 122 of FIG. 1 of the skin disease indication 120 of FIG. 1. The minimum module 912 applies the corrections of the loss module to the analysis of the skin area 704 from the dense+activation relu module 908. The minimum module 912 provides the result 914 for analysis by the acceptable image module 410 of FIG. 4.

The loss module 910 plays an important role in the training process. The loss module 910 punishes the module if it regresses wrong. Regarding the loss and metric, the metric to measure accuracy of the model is mean absolute error (MAE) that is a measure of errors between paired observations expressing the same phenomenon. MAE is calculated as the sum of absolute errors divided by the sample size:

$$MAE = \frac{1}{n}\sum_{j=1}^{n}|y_j - \hat{y}_j| \qquad (3.1)$$

where $y_j$ are the true labels and $\hat{y}_j$ are the corresponding predictions.

It has been discovered that the oops detection module 402 can operate the Inception-ResNet-v2 902 as an artificial intelligence utilizing a convoluted neural network trained with the ImageNet data set to recognize all types of the skin disease result 204 of FIG. 2 that can be identified on the skin surface. The processing of the patient image 114 preserves the overall view while identifying and marking the skin disease result 204 on the skin surface. The loss module 910 can refine the model during execution in order to maintain a high degree of accuracy and improve the process of skin disease identification and analysis.

Figure 10:
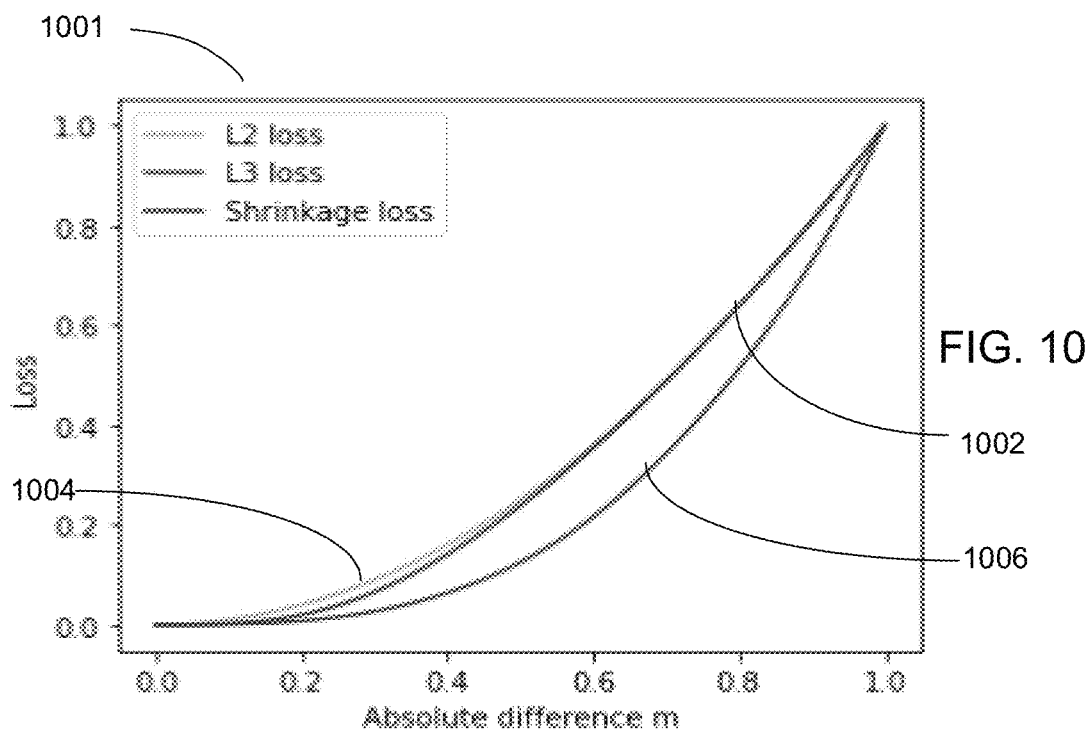
FIG. 10 is an example of the loss comparison chart for the oops detection module in an embodiment.

Referring now to FIG. 10, therein is shown an example of the loss comparison chart 1001 for the oops detection module 402 of FIG. 4 in an embodiment. The compute system 100 of FIG. 1, the skin disease identification module 116 of FIG. 1, or a combination thereof can use the Shrinkage loss 1002 to handle the data imbalance issue in learning deep regression networks. For this task, the compute system 100, the skin disease identification module 116, or a combination thereof can use Shrinkage loss function, which is defined as below:

$$l(y, \hat{y}) = \frac{m^2}{1 + \exp[a \cdot (c - m)]}$$

where m=[y−ŷ], y is the true label and ŷ is the prediction, a and c are hyper-parameters controlling the Shrinkage speed and the localization respectively.

As shown in the example in FIG. 10, the Shrinkage loss 1002 only penalizes the importance of easy samples (when m<0.5) and keeps the loss of hard samples unchanged (when m>0.5) compared to the square loss L2 1004 (with L2=$m^2$). The focal loss L3 1006 (with L3=$m^3$) penalizes both the easy and hard samples.

The compute system 100, the skin disease identification module 116, or a combination thereof set the value of a to be 10 to shrink the weight function quickly and the value of c to be 0.2 to suit for the distribution of m, which ranges from 0 to 1.

Figure 11:
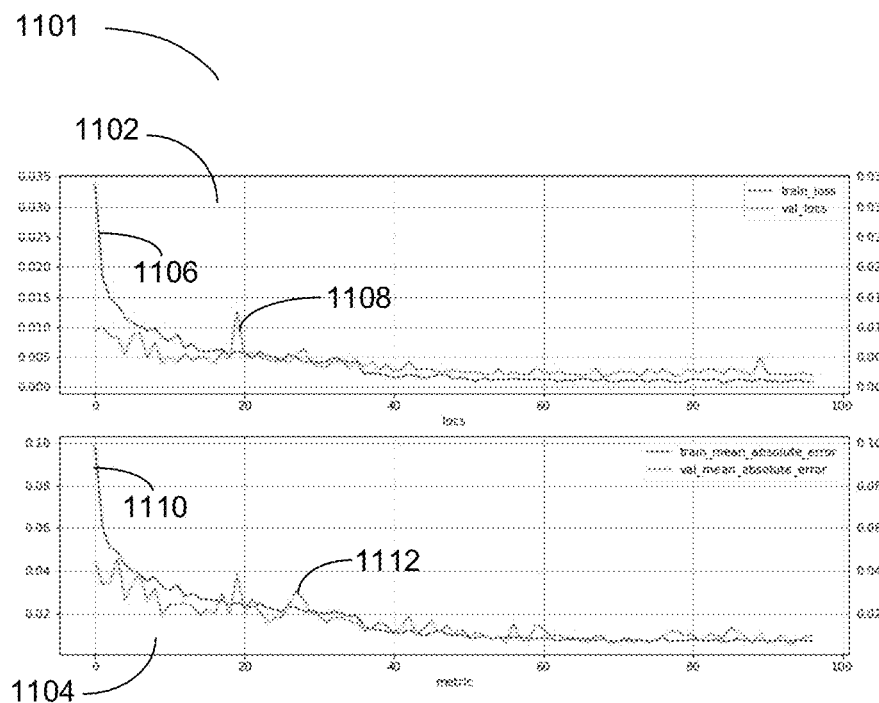
FIG. 11 is an example of the performance chart of the oops detection module in an embodiment.

Referring now to FIG. 11, therein is shown an example of the performance chart 1101 of the oops detection module 402 of FIG. 4 in an embodiment. The compute system 100, the skin disease identification module 116, or a combination thereof can be trained for 95 epochs with nearly 40000 images in each epoch, about 80% data set is reserved for training set and the rest for validation. To measure the accuracy of the model, MAE as equation 3.1 can be utilized. The compute system 100, the skin disease identification module 116, or a combination thereof can obtain 0.01 MAE score on validation. FIG. 11 illustrates for the performance of Oops detection module 402.

A loss chart 1102 indicates the loss function of a training loss 1106 as compared to a verification loss 1108 based on the number of epochs used to train the skin disease identification module 116. As displayed in the loss chart 1102, the verification loss 1108 tracks the training loss 1106 with 0.002 after 95 epochs of training.

An absolute error chart 1104 indicates the mean absolute error of a training error 1110 as compared to a verification error 1112 based on the number of epochs used to train the skin disease identification module 116. As displayed in the absolute error chart 1104, the verification error 1112 tracks the training error 1110 with 0.1 mean absolute error between the predicted values and the absolute values after 95 epochs of training.

Figure 12:
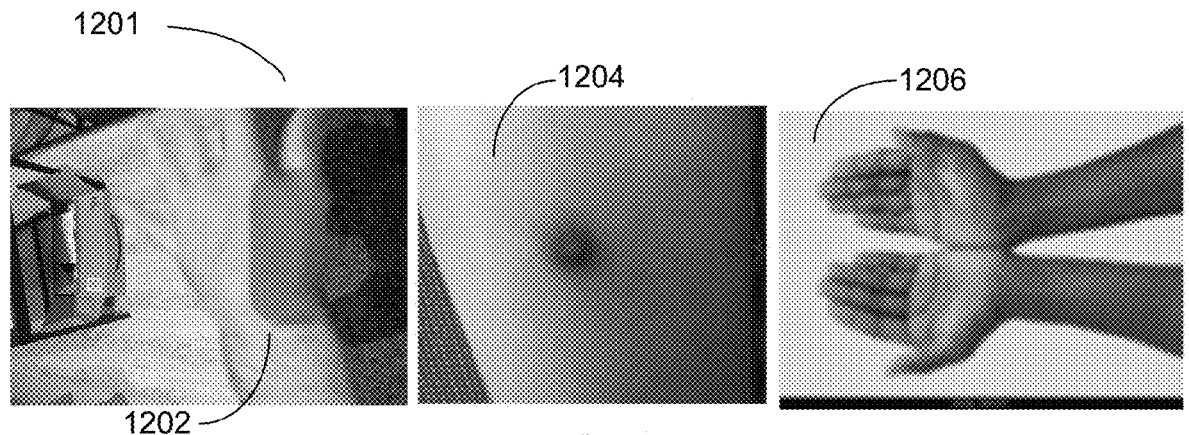
FIG. 12 are examples of patient images classified as blurry images in an embodiment.

Referring now to FIG. 12, therein are shown examples of patient images 114 classified as blurry images 1201 in an embodiment. The images depicted in FIG. 12 are examples used with the image quality check module 404. The dataset includes 5297 images. 86% of them are of good quality, and 14% of them are of bad quality. The image quality check module 404 trained only with good quality images that were modified to transform them into bad quality images did not perform well with real bad quality images. The dataset to train the image quality check module 404 were supplemented to include real bad quality images. The dataset was also supplemented with images to include enough black skin images so that the model does not classify them as "too dark". FIG. 12 are some examples of images of the training dataset.

A first blurry image 1202 is too far away to see details of the skin and a portion of the skin is obstructed by a bandage. A second blurry image 1204 is close enough, but is out of focus, which removes the required detail for analysis by the image quality check module 404. A third blurry image 1206 is too far away and is out of focus making it a useful example of a blurry image for training purposes.

Figure 13:
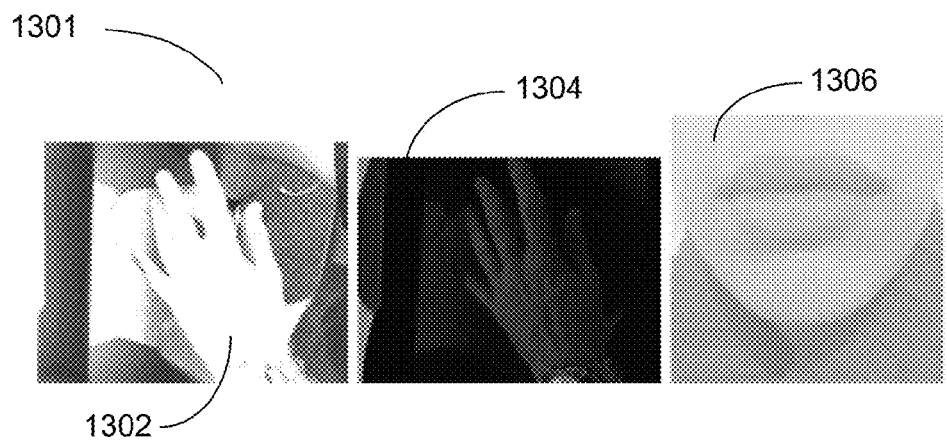
FIG. 13 are examples of patient images classified as bad luminosity images in an embodiment.

Referring now to FIG. 13, therein are shown examples of patient images 114 classified as bad luminosity in an embodiment. FIG. 13 depicts examples of different type of bad luminosity images 1301 used for training the image quality check module 404.

A first bad luminosity image 1302 shows an extremely bright light washes out the details of the skin. A second bad luminosity image 1304 shows too little light to see details of the skin. A third bad luminosity image 1306 shows a colored light washes-out the detail of the skin making the image a good training item for bad luminosity.

Figure 14:
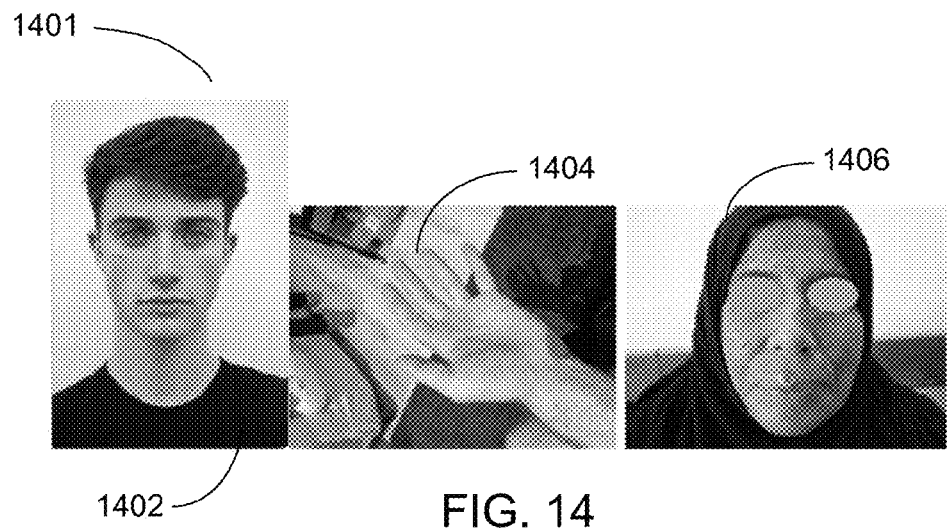
FIG. 14 are examples of patient images classified as acceptable in an embodiment.

Referring now to FIG. 14, therein are shown examples of patient images 114 classified as acceptable in an embodiment. FIG. 14 depict examples of good images 1401 as opposed to bad images to those shown in FIG. 12 or FIG. 13.

A first acceptable image 1402 provides sufficient detail of the face for analysis of the image quality check module 404. A second acceptable image 1404, again provides the correct detail, focus and luminosity to be analyzed correctly. A third acceptable image 1406 is also provided as a good training image for proper focus, luminosity, and detail of the skin for analysis.

Figure 15:
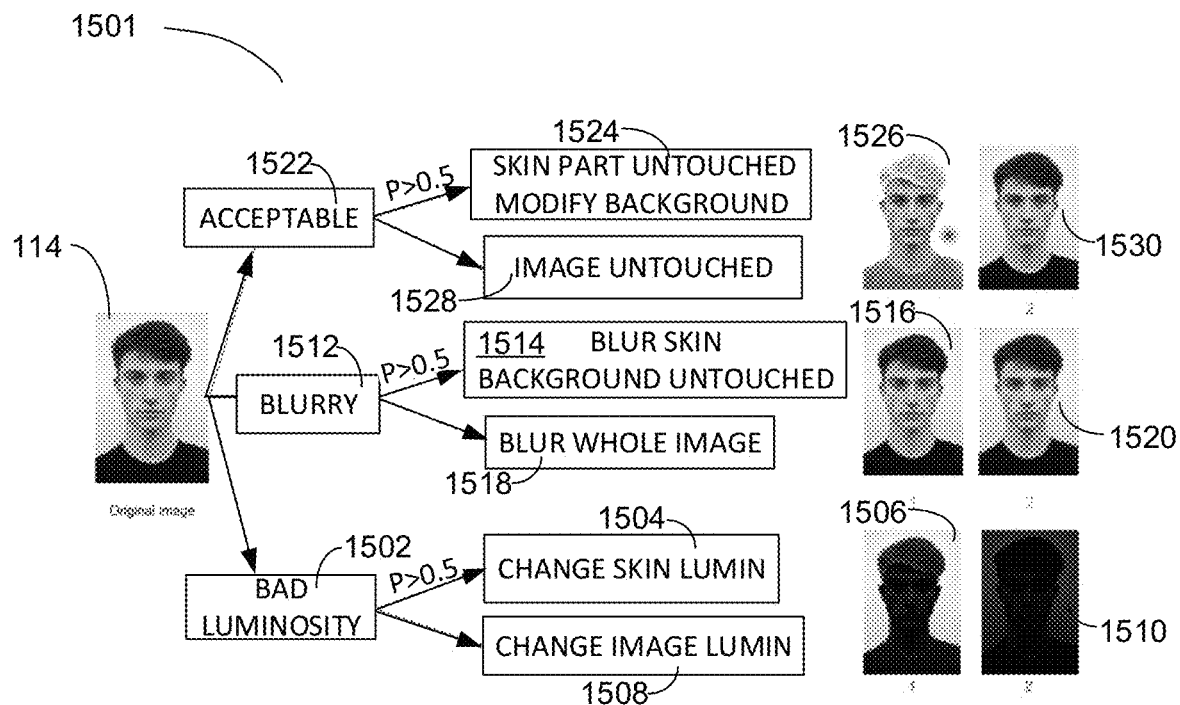
FIG. 15 is an example of a patient image processing with data augmentation in an embodiment.

Referring now to FIG. 15, therein is shown an example of patient image 114 processing with data augmentation 1501 in an embodiment. FIG. 15 depicts examples of a patient image 114 being processed as part of the data augmentation 1501 to the data set for the compute system 100 of FIG. 1, the skin disease identification module 116 of FIG. 1, or a combination thereof. As an example, the patient image 114 is considered a good image. The data augmentation process, in this example, transforms the good image into one or more bad images to generate balanced batch of inputs for the image quality check module 404. The transformations change the good image's luminosity, contrast, add different levels of blur, or a combination thereof. Moreover, to make the model learn to focus on the skin only and not on the background, the compute system 100, the skin disease identification module 116, or a combination thereof trains the model to focus on the skin and not the background, the skin segmentation module 406 to modify the background and keep the skin untouched, or to modify the skin and keep the background untouched.

As a training aide, a bad luminosity block 1502 can change the skin luminosity and the background luminosity in a block 1504 resulting in the high contrast image 1506. The bad luminosity block 1502 can also change the whole image luminosity in a block 1508 resulting in the darkened image 1510. A blurry image block 1512 can blur only the skin part while leaving the background untouched in a block 1514 resulting in the image 1516. The blurry image block 1512 can also blur the entire image in a block 1518 resulting in the image 1520. An acceptable image block 1522 can keep the skin area 602 untouched and blur the non-skin areas of the image in a block 1524, resulting in a first acceptable image 1526. The acceptable image block 1522 can keep the whole image untouched 1528, resulting in a second acceptable image 1530.

It has been discovered that the training of the image quality check module 404 can be trained by manipulating the patient image 114 to intentionally have less that acceptable conditions in a predictable manner by the bad luminosity block 1502 and the blurry image block 1512 for training purposes. This technique can provide balanced analysis of the patient image in normal operation of the image quality check module 404.

Figure 16:
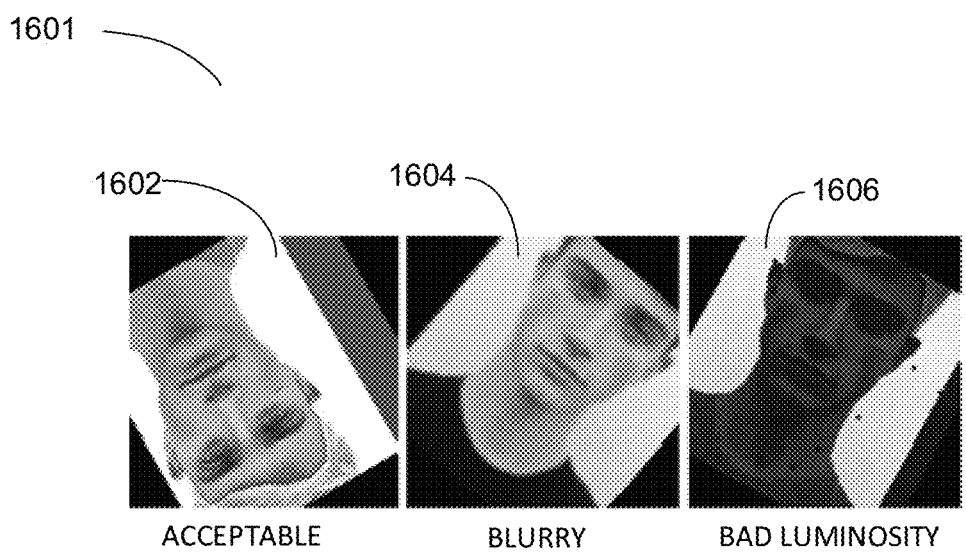
FIG. 16 is an example of a patient image processed with data augmentation and the classification in an embodiment.

Referring now to FIG. 16, therein is shown an example of a patient image 114 processed with data augmentation 1501 and the classification in an embodiment. FIG. 16 depicts example outputs of the data augmentation flow of FIG. 15 such that the compute system 100 of FIG. 1, the skin disease identification module 116 of FIG. 1, or a combination thereof can also perform other data augmentation 1501, such as rotation 1602, transposition 1604, RGB shift 1606, Horizontal and Vertical flip and cutout. The leftmost image 1602 of FIG. 16 is classified as acceptable. The middle image 1604 of FIG. 16 is classified as blurry. The rightmost image 1606 of FIG. 16 is considered bad luminosity.

Figure 17:
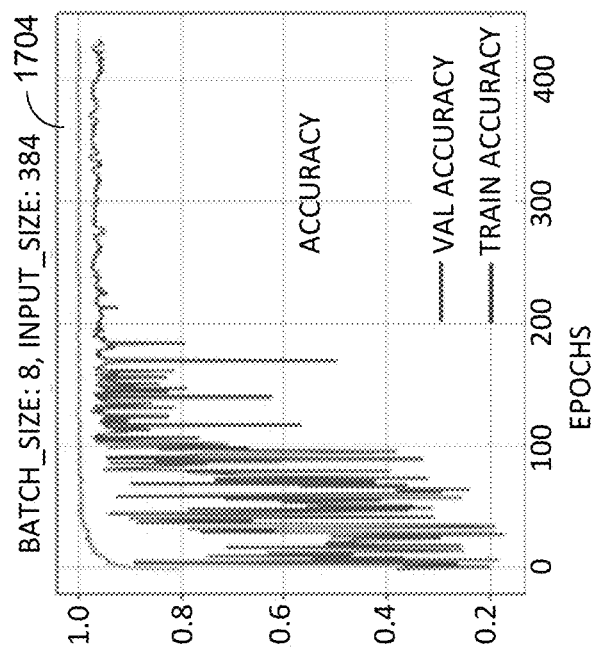
FIG. 17 are examples of performance graphs of the image quality check module in an embodiment.
Figure 17:
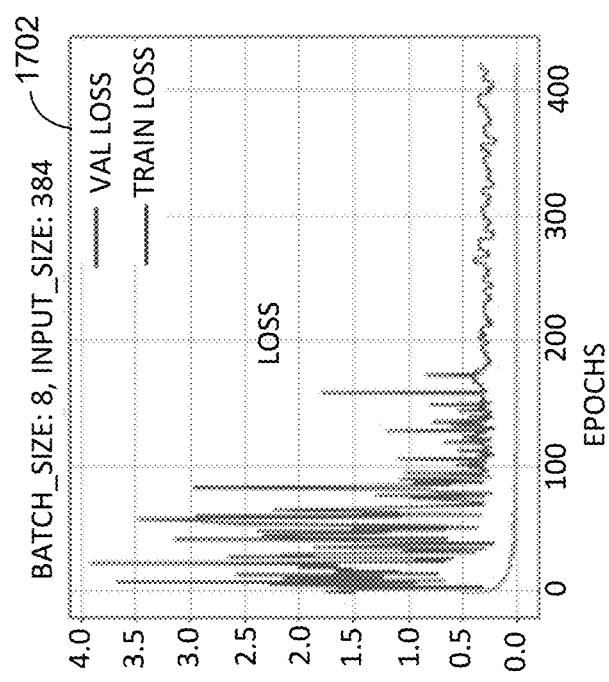

Referring now to FIG. 17, therein are shown examples of performance graphs 1701 of the image quality check module 404 in an embodiment. The performance graphs 1701 include a loss function graph 1702 and an accuracy graph 1704. Regarding the loss function graph 1702 and metrics for the image quality check module 404, a Cross Entropy loss function is utilized and expressed as:

$$\text{Loss} = -\sum_{i=1}^{\substack{output \\ size}} y_i \cdot \log \hat{y}_i \qquad (4.1)$$

The loss function graph 1702 depicted in FIG. 17 is the evolution of the loss function declining as the number of epochs increases. The vertical scale of the loss function graph 1702 is a loss value as determined by equation 4.1. The horizontal scale of the loss function graph 1702 is the number of epochs used to train the image quality check module 404. A single epoch can include 40,000 to 50,000 samples of images having different quality.

The accuracy graph 1704 depicted in FIG. 17 is the evolution of the accuracy metric increasing as the number of epochs increases. The vertical scale of the accuracy graph 1704 is accuracy of the predicted value of image quality as compared to the actual quality of the input image. The horizontal scale of the accuracy graph 1704 is the number of epochs used to train the image quality check module 404.

It has been discovered that the convoluted neural network of the image quality check module 404 can maintain low loss and high degrees of accuracy of validation data after 200 epochs of training data has been processed. The stability of the validated data over the additional 200 epochs demonstrates the ability of the image quality check module 404 to properly determine the quality of the patient images 114.

Figure 18:
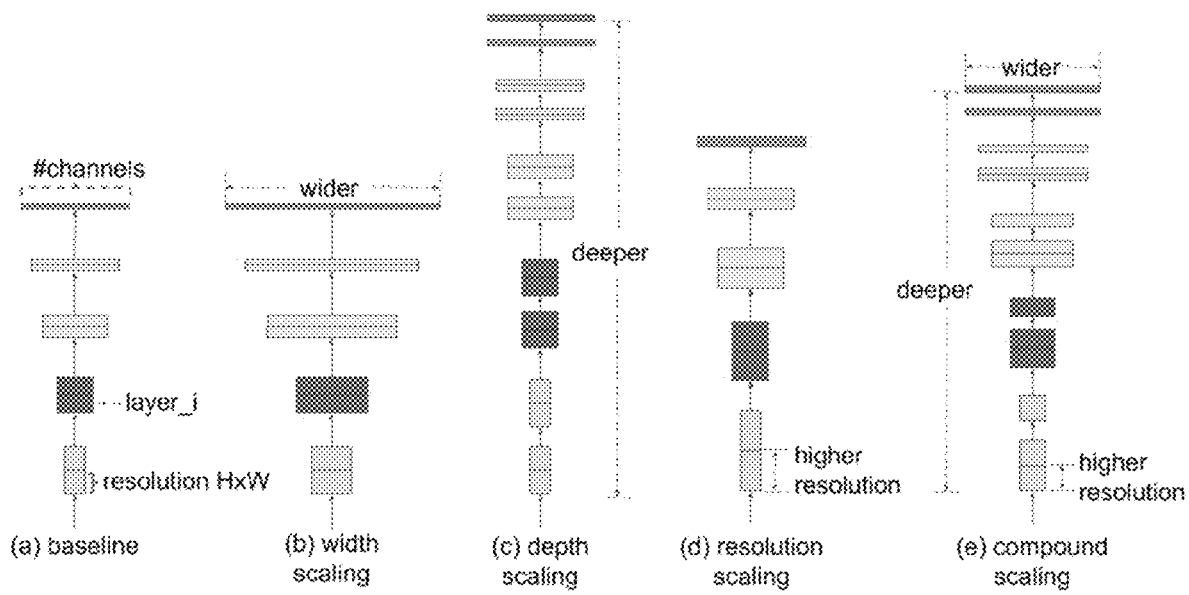
FIG. 18 is an example of functional scaling representation for a portion of the skin segmentation module in an embodiment.

Referring now to FIG. 18, therein is shown an example of functional scaling 1801 representation for a portion of the skin segmentation module 406 in an embodiment. FIG. 18 depicts an example of an implement of the skin segmentation module 406 with EfficientNet. EfficientNet is a convolutional neural network architecture and scaling method that uniformly scales all dimensions of depth, width and resolution of network resources using a compound coefficient.

The EfficientNet scaling of depth of the network can capture richer and more complex features, width of the network can capture the fine-grained features and control the ease of training, and resolution of the network can capture more fine-grained features of the patient mage 114. The EfficientNet can concurrently scale the depth, width, and resolution.

Figure 19:
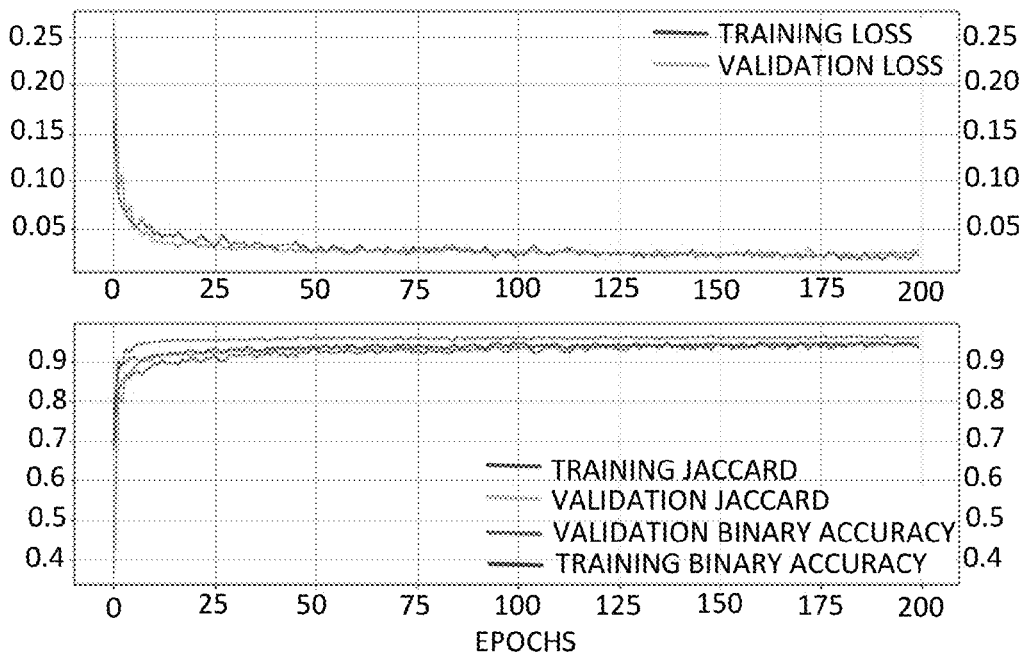
FIG. 19 is an example for the performance graphs of the skin segmentation module in an embodiment.

Referring now to FIG. 19, therein is shown an example for the performance graphs 1901 of the skin segmentation module 406 in an embodiment. As described in FIG. 19, the metric used as an example is the Jaccard score (EQ 2.4). FIG. 19 shows the performance graphs 1901, as an example, up to 200 epochs of training with 0.901 Jaccard score (2.4) and binary accuracy is 0.962 for the skin segmentation module 406. FIG. 19 depicts the Jaccard score, binary accuracy and loss of the skin segmentation module 406.

Figure 20:
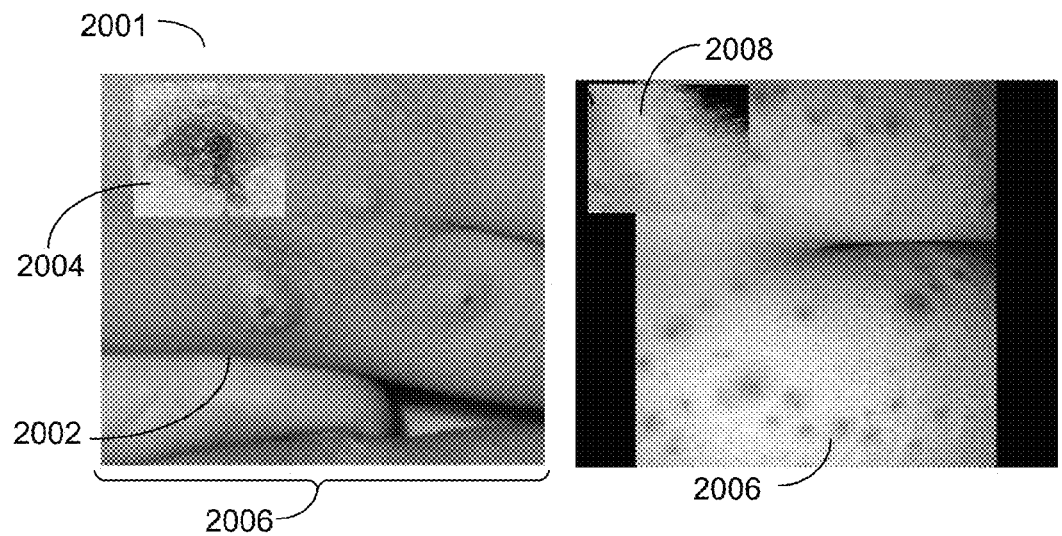
FIG. 20 is an example of a set of synthetic collision images used as validation of the skin segmentation module in an embodiment.

Referring now to FIG. 20, therein is shown an example of a set of synthetic collision images 2001 used as validation of the skin segmentation module 406 of FIG. 4 in an embodiment. FIG. 20 depicts an example of the skin disease segmentation dataset used in training and validation of the skin segmentation module 406. The set of synthetic collision images 2001 represents another way of augmentation in which two images are merged to get one image, this one also helps to enrich dataset especially to the collision lesion cases where there are more than two lesions coexist in one image. Examples of synthetic collision images 2001 include a hand image 2002 showing lesions for analysis by the skin segmentation module 406. A lesion image 2004 is overlayed on the hand image 2002. The resulting image is a synthetic collision image 2006 that can be used to verify the skin segmentation module 406 by verifying that two different types 2008 of the skin disease result 204 of FIG. 2 are reported.

Regarding the training of the skin segmentation module 406, the training dataset includes 901 images including variety in skin disease severity, resolution that varies from smart-phone images to professional images, views that include close-up and wide shots, and skin tone including lighter skin to darker skin. These images are split into 5 folds of approximately 180 images each, where 1 fold is designated for validation and the other four for training. Since the compute system 100 of FIG. 1, the skin disease identification module 116 of FIG. 1, or a combination thereof can segment skin disease and skin disease-like objects, the compute system 100, the skin disease identification module 116, or a combination thereof does not required doctors to do the job.

Regarding data augmentation 1501 for the skin segmentation module 406, the crop segment module 408 can apply techniques of the data augmentation 1401 to both the patient images 114 and the synthetic collision image 2006. Examples of the techniques include random rotation to an angle between –30 and 30 degrees, random flipping, random changing of brightness, random re-scaling between 0.7 to 1.3 times original size, and crop to the model size, or a combination thereof.

Figure 21:
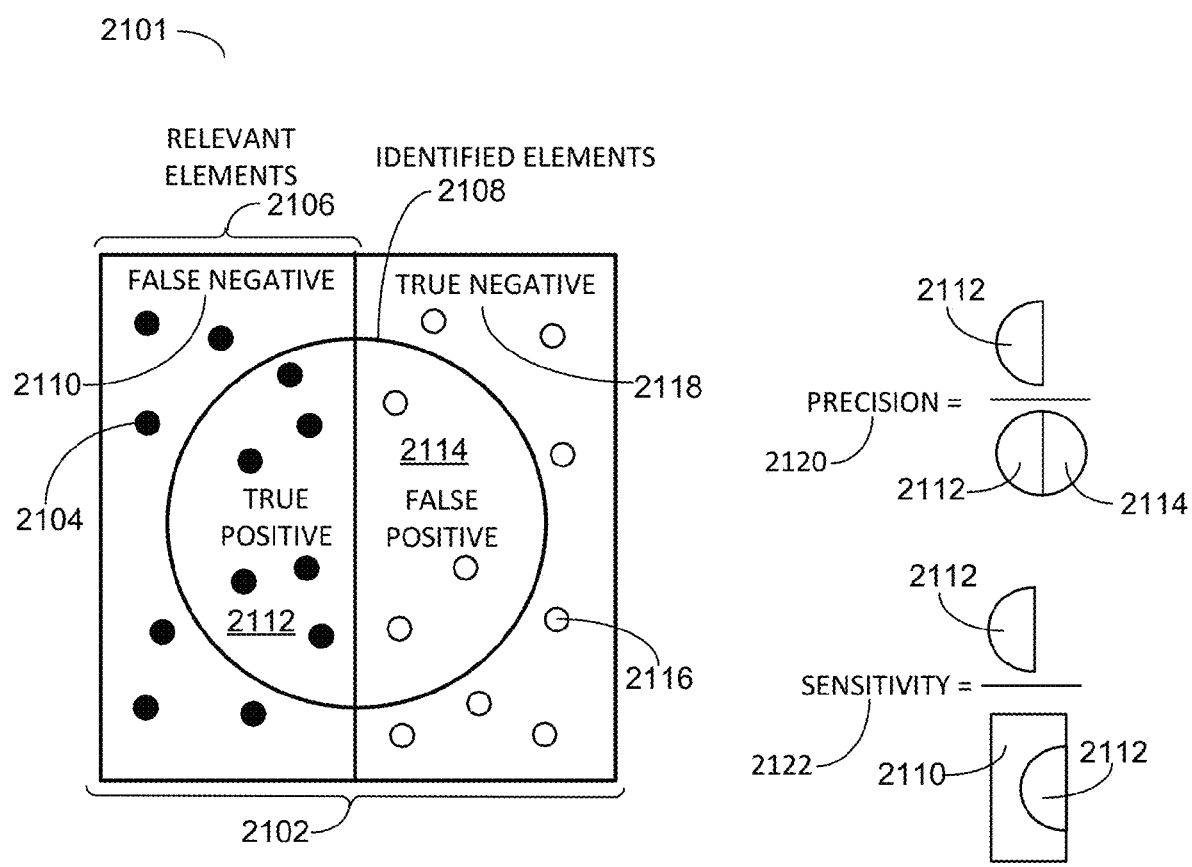
FIG. 21 is an example of a Ven diagram for a determination of the skin segmentation module in an embodiment.

Referring now to FIG. 21, therein is shown an example of a Venn diagram 2101 for a determination of the skin segmentation module 406 of FIG. 4 in an embodiment. The Venn diagram 2101 for a determination of the skin segmentation module 406 depicts a range 2102 of skin conditions 2104. The skin segmentation module 406 can process relevant elements 2106 to identify the skin conditions 2104.

The skin segmentation module 406 can process identified elements 2108, shown within the circle. The relevant elements 2106 that fall outside the identified elements 2108 are defined as false negatives 2110. The false negatives 2110 are the skin conditions 2104 that were not identified by the skin segmentation module 406. A set of false positives 2114 can be non-disease images 2116 that were incorrectly identified as the skin disease 2104. A set of true negatives 2118 can be the non-disease images 2116 that were accurately assessed as having none of the skin disease 2104.

A value of precision score 2120 can be calculated by dividing the true positives 2112 by the identified elements 2108 that includes the true positives 2112 and the false positives 2114. The precision score 2120 can represent a measure of accuracy for the skin segmentation module 406. A value of sensitivity score 2122 can be calculated by dividing the true positives 2112 by the relevant elements 2106 that includes the true positives 2112 and the false negatives 2110.

It is understood that the precision score 2120 of the compute system 100 of FIG. 1, the skin disease identification module 116 of FIG. 1, or a combination thereof is shown in the accuracy graph 1704 of FIG. 17 to be 0.91 beyond 200 epochs of training. By way of an example, suppose that the skin segmentation module 406 has to analyze 1000 images, with 10 images labelled "Disease A" showing the skin disease 2104 and 900 images labelled "no disease A" as the non-disease image 2116. The skin segmentation module 406 can select the identified elements 2108 including 45 images predicted as "Disease A", none of the identified elements 2108 have real disease and are the true positive 2112. The other 36 images are actually the non-disease images 2116, which are wrongly predicted to be "Disease A" are flagged as false positive 2114. On the other hand, only 1 image of the skin disease 2104, with real disease is missed and declared as the false positive 2114 and 864 images with no label are correctly identified as the true negative 2118. The precision score 2120 is then computed as 9/45=0.2 and the sensitivity score 2122 as 9/10=0.9.

Figure 22:
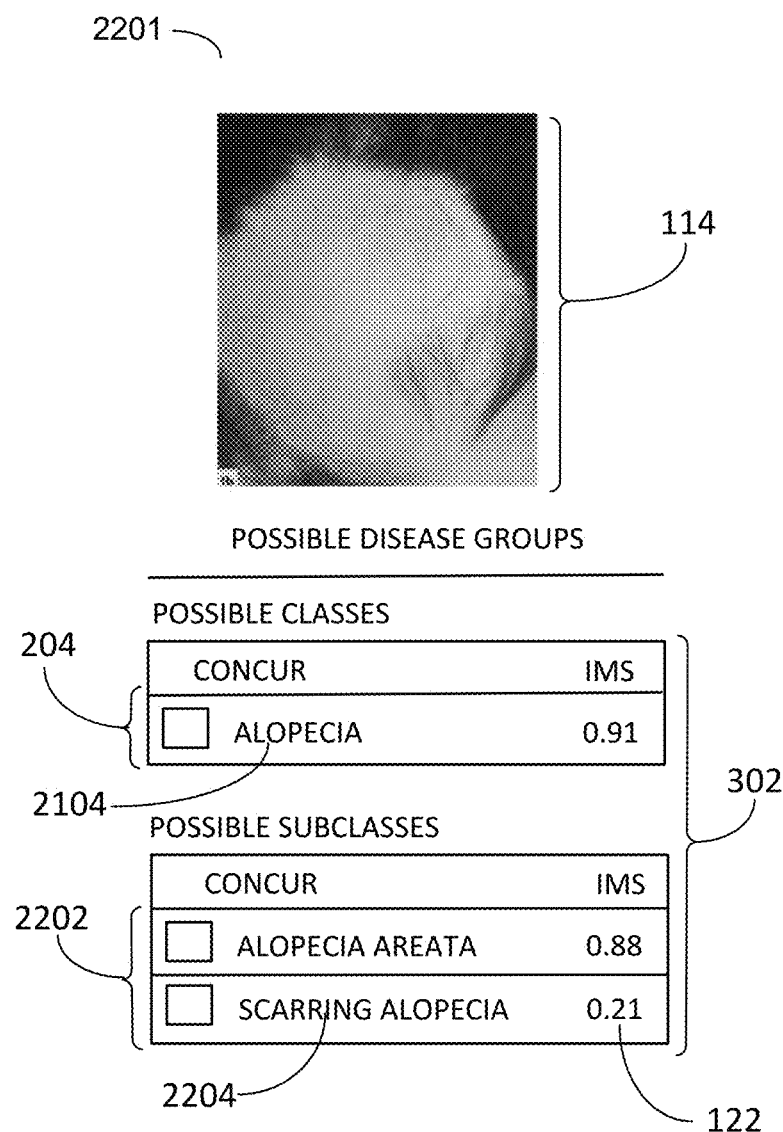
FIG. 22 is an example of a disease identification display from an input image in a further embodiment.

Referring now to FIG. 22, therein is shown an example of a disease identification display 2201 from an input image 114 in a further embodiment. FIG. 22 can depict the patient image 114 analyzed by the compute system 100 of FIG. 1, the skin disease identification module 116 of FIG. 1, or a combination thereof to produce the skin disease identification list 302. The skin disease identification list 302 can include the skin disease result 204 and a subclass list 2202 of the disease subclasses 2204.

The skin disease result 204 can identify a major category of the skin disease 2104, which can omit additional information that was identified by the skin disease identification module 116. The addition of the subclass list 2202 of the disease subclasses 2204 can provide the additional information that can assist the clinician in formulating a plan of action to address the skin disease 2104. By observing the image matching score 122, the highest probability of the disease subclass 2204 can be determined. The addition of the subclass list 2202 can provide a more complete description of the skin disease 2104 present in the patient image 114.

Figure 23:
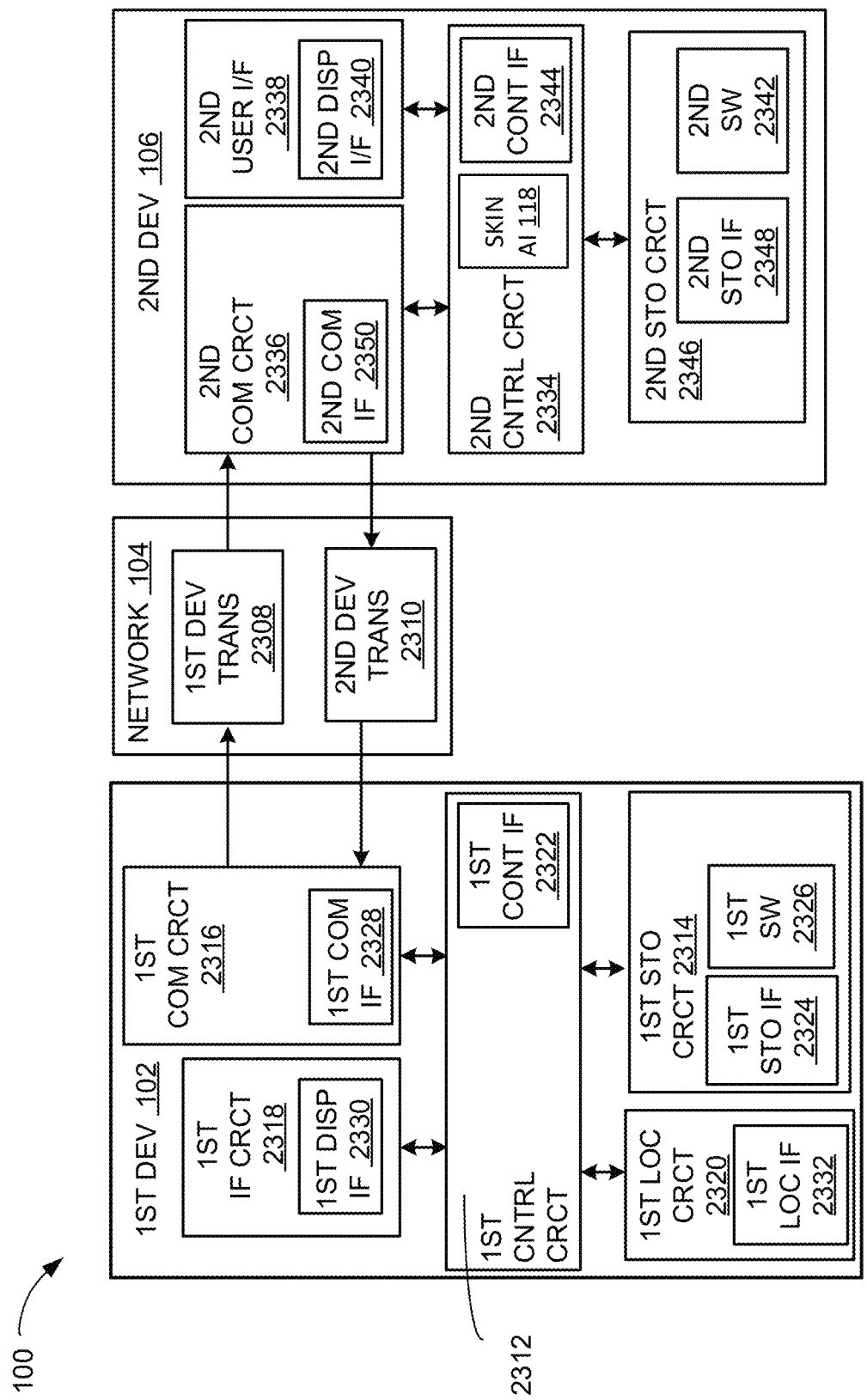
FIG. 23 is an exemplary block diagram of the compute system in an embodiment.

Referring now to FIG. 23, therein is shown an exemplary block diagram of the compute system 100 in an embodiment. The compute system 100 can include the first device 102, the network 104, and the second device 106. The first device 102 can send information in a first device transmission 2308 over the network 104 to the second device 106. The second device 106 can send information in a second device transmission 2310 over the network 104 to the first device 102 or the vehicle 201 of FIG. 2.

For illustrative purposes, the compute system 100 is shown with the first device 102 as a client device, although it is understood that the compute system 100 can include the first device 102 as a different type of device.

Also, for illustrative purposes, the compute system 100 is shown with the second device 106 as a server, although it is understood that the compute system 100 can include the second device 106 as a different type of device. For example, the second device 106 can be a client device. By way of an example, the compute system 100 can be implemented entirely on the first device 102.

Also, for illustrative purposes, the compute system 100 is shown with interaction between the first device 102 and the second device 106. However, it is understood that the first device 102 can be a part of or the entirety of a diagnostic tool, a smart phone, a medical instrument, or a combination thereof. Similarly, the second device 106 can similarly interact with the first device 102 representing the diagnostic tool, the smart phone, the medical instrument, or a combination thereof.

For brevity of description in this embodiment of the present invention, the first device 102 will be described as a client device and the second device 106 will be described as a server device. The embodiment of the present invention is not limited to this selection for the type of devices. The selection is an example of an embodiment of the present invention.

The first device 102 can include a first control circuit 2312, a first storage circuit 2314, a first communication circuit 2316, a first interface circuit 2318, and a first location circuit 2320. The first control circuit 2312 can include a first control interface 2322. The first control circuit 2312 can execute a first software 2326 to provide the intelligence of the compute system 100.

The first control circuit 2312 can be implemented in a number of different manners. For example, the first control circuit 2312 can be a processor, an application specific integrated circuit (ASIC) an embedded processor, a microprocessor, a hardware control logic, a hardware finite state machine (FSM), a digital signal processor (DSP), or a combination thereof. The first control interface 2322 can be used for communication between the first control circuit 2312 and other functional units or circuits in the first device 102. The first control interface 2322 can also be used for communication that is external to the first device 102.

The first control interface 2322 can receive information from the other functional units/circuits or from external sources, or can transmit information to the other functional units/circuits or to external destinations. The external sources and the external destinations refer to sources and destinations external to the first device 102.

The first control interface 2322 can be implemented in different ways and can include different implementations depending on which functional units/circuits or external units/circuits are being interfaced with the first control interface 2322. For example, the first control interface 2322 can be implemented with a pressure sensor, an inertial sensor, a microelectromechanical system (MEMS), optical circuitry, waveguides, wireless circuitry, wireline circuitry, or a combination thereof.

The first storage circuit 2314 can store the first software 2326. The first storage circuit 2314 can also store the relevant information, such as data representing incoming images, data representing previously presented image, sound files, or a combination thereof.

The first storage circuit 2314 can be a volatile memory, a nonvolatile memory, an internal memory, an external memory, or a combination thereof. For example, the first storage circuit 2314 can be a nonvolatile storage such as non-volatile random-access memory (NVRAM), Flash memory, disk storage, or a volatile storage such as static random-access memory (SRAM).

The first storage circuit 2314 can include a first storage interface 2324. The first storage interface 2324 can be used for communication between the first storage circuit 2314 and other functional units or circuits in the first device 102. The first storage interface 2324 can also be used for communication that is external to the first device 102.

The first storage interface 2324 can receive information from the other functional units/circuits or from external sources, or can transmit information to the other functional units/circuits or to external destinations. The external sources and the external destinations refer to sources and destinations external to the first device 102. The first storage interface 2324 can receive input from and source data to the skin disease identification module 116.

The first storage interface 2324 can include different implementations depending on which functional units/circuits or external units/circuits are being interfaced with the first storage circuit 2314. The first storage interface 2324 can be implemented with technologies and techniques similar to the implementation of the first control interface 2322.

The first communication circuit 2316 can enable external communication to and from the first device 102. For example, the first communication circuit 2316 can permit the first device 102 to communicate with the second device 106 and the network 104.

The first communication circuit 2316 can also function as a communication hub allowing the first device 102 to function as part of the network 104 and not limited to be an endpoint or terminal circuit to the network 104. The first communication circuit 2316 can include active and passive components, such as microelectronics or an antenna, for interaction with the network 104.

The first communication circuit 2316 can include a first communication interface 2328. The first communication interface 2328 can be used for communication between the first communication circuit 2316 and other functional units or circuits in the first device 102. The first communication interface 2328 can receive information from the second device 106 for distribution to the other functional units/circuits or can transmit information to the other functional units or circuits.

The first communication interface 2328 can include different implementations depending on which functional units or circuits are being interfaced with the first communication circuit 2316. The first communication interface 2328 can be implemented with technologies and techniques similar to the implementation of the first control interface 2322.

The first interface circuit 2318 allows the user 112 of FIG. 1 to interface and interact with the first device 102. The first interface circuit 2318 can include an input device and an output device. Examples of the input device of the first interface circuit 2318 can include a keypad, a touchpad, soft-keys, a keyboard, a camera, a microphone, an infrared sensor for receiving remote signals, or any combination thereof to provide data and communication inputs.

The first interface circuit 2318 can include a first display interface 2330. The first display interface 2330 can include an output device. The first display interface 2330 can include a projector, a video screen, a touch screen, a speaker, a microphone, a keyboard, and combinations thereof.

The first control circuit 2312 can operate the first interface circuit 2318 to display information generated by the compute system 100 and receive input from the user 112. The first control circuit 2312 can also execute the first software 2326 for the other functions of the compute system 100, including receiving location information from the first location circuit 2320. The first control circuit 2312 can further execute the first software 2326 for interaction with the network 104 via the first communication circuit 2316. The first control circuit 2312 can operate the skin disease identification module 116 of FIG. 1, or portions thereof.

The first control circuit 2312 can also receive location information from the first location circuit 2320. The first control circuit 2312 can operate the skin disease identification module 116.

The first location circuit 2320 can be implemented in many ways. For example, the first location circuit 2320 can function as at least a part of the global positioning system, an inertial compute system, a cellular-tower location system, a gyroscope, or any combination thereof. Also, for example, the first location circuit 2320 can utilize components such as an accelerometer, gyroscope, or global positioning system (GPS) receiver.

The first location circuit 2320 can include a first location interface 2332. The first location interface 2332 can be used for communication between the first location circuit 2320 and other functional units or circuits in the first device 102, including the environmental sensors 210.

The first location interface 2332 can receive information from the other functional units/circuits or from external sources, or can transmit information to the other functional units/circuits or to external destinations. The external sources and the external destinations refer to sources and destinations external to the first device 102. The first location interface 2332 can receive the global positioning location from the global positioning system (not shown).

The first location interface 2332 can include different implementations depending on which functional units/circuits or external units/circuits are being interfaced with the first location circuit 2320. The first location interface 2332 can be implemented with technologies and techniques similar to the implementation of the first control circuit 2312.

The second device 106 can be optimized for implementing an embodiment of the present invention in a multiple device embodiment with the first device 102. The second device 106 can provide the additional or higher performance processing power compared to the first device 102. The second device 106 can include a second control circuit 2334, a second communication circuit 2336, a second user interface 2338, and a second storage circuit 2346.

The second user interface 2338 allows an operator (not shown) to interface and interact with the second device 106. The second user interface 2338 can include an input device and an output device. Examples of the input device of the second user interface 2338 can include a keypad, a touchpad, soft-keys, a keyboard, a camera, a microphone, or any combination thereof to provide data and communication inputs. Examples of the output device of the second user interface 2338 can include a second display interface 2340. The second display interface 2340 can include a display, a projector, a video screen, a speaker, or any combination thereof.

The second control circuit 2334 can execute a second software 2342 to provide the intelligence of the second device 106 of the compute system 100. The second software 2342 can operate in conjunction with the first software 2326. The second control circuit 2334 can provide additional performance compared to the first control circuit 2312. The second control circuit 2334 can control the skin disease AI 118.

The second control circuit 2334 can operate the second user interface 2338 to display information. The second control circuit 2334 can also execute the second software 2342 for the other functions of the compute system 100, including operating the second communication circuit 2336 to communicate with the first device 102 over the network 104.

The second control circuit 2334 can be implemented in a number of different manners. For example, the second control circuit 2334 can be a processor, an embedded processor, a microprocessor, hardware control logic, a hardware finite state machine (FSM), a digital signal processor (DSP), or a combination thereof.

The second control circuit 2334 can include a second control interface 2344. The second control interface 2344 can be used for communication between the second control circuit 2334 and other functional units or circuits in the second device 106. The second control interface 2344 can also be used for communication that is external to the second device 106.

The second control interface 2344 can receive information from the other functional units/circuits or from external sources, or can transmit information to the other functional units/circuits or to external destinations. The external sources and the external destinations refer to sources and destinations external to the second device 106.

The second control interface 2344 can be implemented in different ways and can include different implementations depending on which functional units/circuits or external units/circuits are being interfaced with the second control interface 2344. For example, the second control interface 2344 can be implemented with a pressure sensor, an inertial sensor, a microelectromechanical system (MEMS), optical circuitry, waveguides, wireless circuitry, wireline circuitry, or a combination thereof.

The second storage circuit 2346 can store the second software 2342. The second storage circuit 2346 can also store the information such as data representing incoming images, data representing previously presented image, sound files, or a combination thereof. The second storage circuit 2346 can be sized to provide the additional storage capacity to supplement the first storage circuit 2314.

For illustrative purposes, the second storage circuit 2346 is shown as a single element, although it is understood that the second storage circuit 2346 can be a distribution of storage elements. Also, for illustrative purposes, the compute system 100 is shown with the second storage circuit 2346 as a single hierarchy storage system, although it is understood that the compute system 100 can include the second storage circuit 2346 in a different configuration. For example, the second storage circuit 2346 can be formed with different storage technologies forming a memory hierarchal system including different levels of caching, main memory, rotating media, or off-line storage.

The second storage circuit 2346 can be a controller of a volatile memory, a nonvolatile memory, an internal memory, an external memory, or a combination thereof. For example, the second storage circuit 2346 can be a controller of a nonvolatile storage such as non-volatile random-access memory (NVRAM), Flash memory, disk storage, or a volatile storage such as static random access memory (SRAM).

The second storage interface 2348 can receive information from the other functional units/circuits or from external sources, or can transmit information to the other functional units/circuits or to external destinations. The external sources and the external destinations refer to sources and destinations external to the second device 106.

The second storage interface 2348 can include different implementations depending on which functional units/circuits or external units/circuits are being interfaced with the second storage circuit 2346. The second storage interface 2348 can be implemented with technologies and techniques similar to the implementation of the second control interface 2344.

The second communication circuit 2336 can enable external communication to and from the second device 106. For example, the second communication circuit 2336 can permit the second device 106 to communicate with the first device 102 over the network 104.

The second communication circuit 2336 can also function as a communication hub allowing the second device 106 to function as part of the network 104 and not limited to be an endpoint or terminal unit or circuit to the network 104. The second communication circuit 2336 can include active and passive components, such as microelectronics or an antenna, for interaction with the network 104.

The second communication circuit 2336 can include a second communication interface 2350. The second communication interface 2350 can be used for communication between the second communication circuit 2336 and other functional units or circuits in the second device 106. The second communication interface 2350 can receive information from the other functional units/circuits or can transmit information to the other functional units or circuits.

The second communication interface 2350 can include different implementations depending on which functional units or circuits are being interfaced with the second communication circuit 2336. The second communication interface 2350 can be implemented with technologies and techniques similar to the implementation of the second control interface 2344.

The second communication circuit 2336 can couple with the network 104 to send information to the first device 102. The first device 102 can receive information in the first communication circuit 2316 from the second device transmission 2310 of the network 104. The compute system 100 can be executed by the first control circuit 2312, the second control circuit 2334, or a combination thereof. For illustrative purposes, the second device 106 is shown with the partition containing the second user interface 2338, the second storage circuit 2346, the second control circuit 2334, and the second communication circuit 2336, although it is understood that the second device 106 can include a different partition. For example, the second software 2342 can be partitioned differently such that some or all of its function can be in the second control circuit 2334 and the second communication circuit 2336. Also, the second device 106 can include other functional units or circuits not shown in FIG. 61 for clarity.

The functional units or circuits in the first device 102 can work individually and independently of the other functional units or circuits. The first device 102 can work individually and independently from the second device 106 and the network 104.

The functional units or circuits in the second device 106 can work individually and independently of the other functional units or circuits. The second device 106 can work individually and independently from the first device 102 and the network 104.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

For illustrative purposes, the compute system 100 is described by operation of the first device 102 and the second device 106. It is understood that the first device 102 and the second device 106 can operate any of the modules and functions of the compute system 100.

Figure 24:
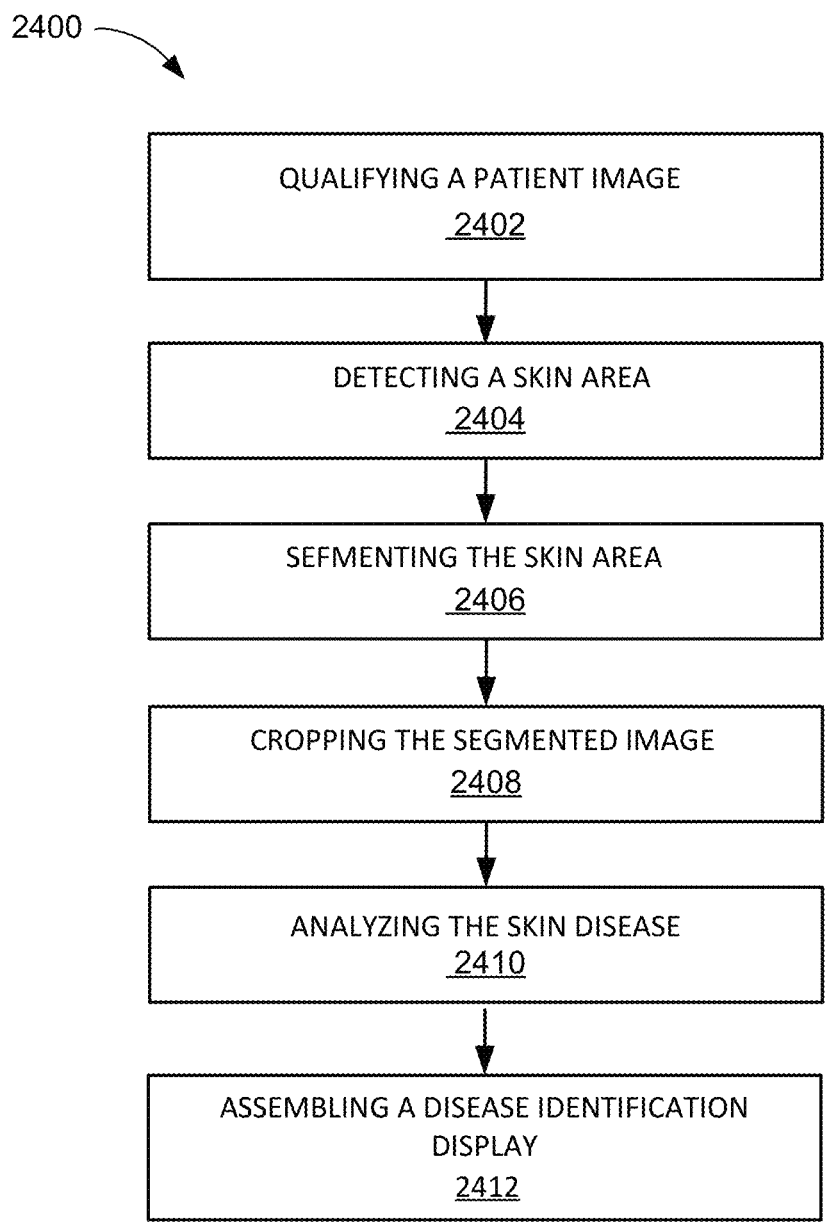
FIG. 24 is a flow chart of a method of operation of a compute system in an embodiment of the present invention.

Referring now to FIG. 24, therein is shown a flow chart of a method 2400 of operation of a compute system 100 of FIG. 1 in an embodiment of the present invention. The method 2400 includes: qualifying a patient image for analyzing a suspected skin condition in a block 2402; detecting a skin area in the patient image in a block 2404; segmenting the skin area into a segmented image including the suspected skin condition in a block 2406; cropping the segmented image to form a cropped image including the suspected skin condition at a center of the cropped image in a block 2408; analyzing the skin disease to identify a skin disease result and a disease subclass from the cropped image in a block 2410; and assembling a disease identification display including the patient image, a skin disease indication, an image match score, and the disease subclass for displaying on a device in a block 2412.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:
   qualifying a patient image for analyzing for a suspected skin condition;
   detecting a skin area in the patient image;
   segmenting the skin area into a segmented image including the suspected skin condition;
   cropping the segmented image to form a cropped image including the suspected skin condition at a center of the cropped image;
   analyzing the suspected skin condition to identify a skin disease result and a disease subclass from the cropped image;
   calculating an image score for each of the skin disease result and the disease subclass identified in the patient image; and
   assembling a disease identification display including the patient image, a skin disease indication, the image match score, and the disease subclass for displaying on a device.

2. The method as claimed in claim 1 wherein qualifying the patient image includes identifying the skin area to be greater than 20% of the patient image.

3. The method as claimed in claim 1 wherein qualifying the patient image includes verifying a blurry metric and a bad luminosity metric.

4. The method as claimed in claim 1 further comprising generating a skin disease identification list of the skin disease result and a subclass list including one or more of the disease subclass.

5. The method as claimed in claim 1 wherein analyzing the suspected skin condition includes performing a disease classification for generating a skin disease diagnosis.

6. The method as claimed in claim 1 wherein assembling the disease identification display includes generating a skin disease identification list with a subclass list of the disease subclass.

7. The method as claimed in claim 1 further comprising generating a retake image message for the patient image with less than 20% of the skin area, has a blurry metric greater than a blurry threshold, with a luminosity metric greater than a luminosity threshold, or a combination thereof.

8. A compute system comprising:
   a control circuit, including a processor, configured to:
      qualify a patient image to analyze for a suspected skin condition;
      detect a skin area in the patient image;
      segment the skin area into a segmented image including the suspected skin condition;
      crop the segmented image to form a cropped image including the suspected skin condition at a center of the cropped image;
      analyze the suspected skin condition to identify a skin disease result and a disease subclass from the cropped image;
      calculate an image score for each of the skin disease result and the disease subclass identified in the patient image; and
   a communication circuit, coupled to the control circuit, configured to assemble a disease identification display including the patient image, a skin disease indication, the image match score, and the disease subclass for displaying on a device.

9. The system as claimed in claim 8 wherein the control circuit is further configured to qualify a patient image including identify the skin area to be greater than 20% of the patient image.

10. The system as claimed in claim 8 wherein the control circuit is further configured to qualify a patient image including compare a blurry metric to a blurry threshold and a bad luminosity metric to a luminosity threshold.

11. The system as claimed in claim 8 wherein the control circuit is further configured to generating a skin disease identification list of the skin disease result and a subclass list that includes one or more of the disease subclass.

12. The system as claimed in claim 8 wherein the control circuit is further configured to analyze the suspected skin condition including perform a disease classification to generate a skin disease diagnosis.

13. The system as claimed in claim 8 wherein the control circuit is further configured to assemble the disease identification display including generate a skin disease identification list with a subclass list of the disease subclass.

14. The system as claimed in claim 8 wherein the control circuit is further configured to generate a retake image message for the patient image with less than 20% of the skin area, has a blurry metric greater than a blurry threshold, with a luminosity metric greater than a luminosity threshold, or a combination thereof.

15. A non-transitory computer readable medium including instructions for a compute system comprising:
   qualifying a patient image for analyzing a suspected skin condition;
   detecting a skin area in the patient image;
   segmenting the skin area into a segmented image including the suspected skin condition;
   cropping the segmented image to form a cropped image including the suspected skin condition at a center of the cropped image;
   analyzing the suspected skin condition to identify a skin disease result and a disease subclass;
   calculating an image score for each of the skin disease result and the disease subclass identified in the patient image; and
   assembling a disease identification display including the patient image, a skin disease indication, the image match score, and the disease subclass for displaying on a device.

16. The non-transitory computer readable medium as claimed in claim 15 wherein qualifying the patient image includes identifying the skin area to be greater than 20% of the patient image.

17. The non-transitory computer readable medium as claimed in claim 15 wherein qualifying the patient image includes comparing a blurry metric to a blurry threshold and a bad luminosity metric to a luminosity threshold.

18. The non-transitory computer readable medium as claimed in claim 15 further comprising generating a skin disease identification list of the skin disease result and a subclass list including one or more of the disease subclass.

19. The non-transitory computer readable medium as claimed in claim 15 wherein analyzing the suspected skin condition includes performing a disease classification for generating a skin disease diagnosis.

20. The non-transitory computer readable medium as claimed in claim 15 further comprising generating a retake image message for the patient image with less than 20% of the skin area, has a blurry metric greater than a blurry threshold, has a luminosity metric greater than a luminosity threshold, or a combination thereof.

\* \* \* \* \*